United States Patent
Xu et al.

(10) Patent No.: US 11,352,336 B2
(45) Date of Patent: Jun. 7, 2022

(54) BI-PHASIC CONTINUOUS-FLOW TUBULAR REACTOR AND HETEROGENEOUS CATALYSTS PREPARATION METHOD FOR PRODUCTION OF 5-HYDROXYMETHYL FURFURAL

(71) Applicant: THE UNIVERSITY OF WESTERN ONTARIO, London (CA)

(72) Inventors: Chunbao Xu, London (CA); Sadra Souzanchi, London (CA); Tirumala Venkateswara Rao Kasanneni, London (CA); Zhongshun Yuan, London (CA)

(73) Assignee: THE UNIVERSITY OF WESTERN ONTARIO, London (CA)

( * ) Notice: Subject to any disclaimer, the term of this patent is extended or adjusted under 35 U.S.C. 154(b) by 60 days.

(21) Appl. No.: 16/621,632

(22) PCT Filed: Jun. 29, 2017

(86) PCT No.: PCT/CA2017/050792
§ 371 (c)(1),
(2) Date: Dec. 11, 2019

(87) PCT Pub. No.: WO2019/000069
PCT Pub. Date: Jan. 3, 2019

(65) Prior Publication Data
US 2020/0172500 A1    Jun. 4, 2020

(51) Int. Cl.
*C07D 307/50* (2006.01)
*B01J 8/00* (2006.01)
*B01J 8/06* (2006.01)
*B01J 23/20* (2006.01)
*B01J 27/18* (2006.01)
*B01J 27/195* (2006.01)
*B01J 31/10* (2006.01)

(52) U.S. Cl.
CPC ............ *C07D 307/50* (2013.01); *B01J 8/001* (2013.01); *B01J 8/065* (2013.01); *B01J 8/067* (2013.01); *B01J 23/20* (2013.01); *B01J 27/1813* (2013.01); *B01J 27/195* (2013.01); *B01J 31/10* (2013.01); *B01J 2208/00212* (2013.01); *B01J 2208/00539* (2013.01); *B01J 2231/763* (2013.01); *B01J 2531/002* (2013.01)

(58) Field of Classification Search
CPC ......... C07D 307/50; B01J 8/001; B01J 8/065; B01J 8/067; B01J 23/20; B01J 27/1818; B01J 27/195; B01J 31/10; B01J 2208/00212; B01J 2208/00539; B01J 2231/763; B01J 2231/002
See application file for complete search history.

(56) References Cited

U.S. PATENT DOCUMENTS 7,317,116 B2 *  1/2008  Sanborn .................. C07C 51/00
                                                    549/483

FOREIGN PATENT DOCUMENTS

WO        2007146636 A1    12/2007

OTHER PUBLICATIONS

Zhao et al., High selective production of 5-hydroymethylfurfural from fructose by a solid heteropolyacid catalyst. Fuel, Jun. 1, 2011 vol. 90(6), pp. 2289-2293.
Ordomsky et al., "Glucose dehydration to 5-hydroxymethylfurfural in a biphasic system over solid acid foams". ChemSusChem, Sep. 14, 2013 vol. 6(9), pp. 1697-1707.
Ordomsky et al., "Glucose dehydration to 5-hydroxymethylfurfural over phosphate catalysts". Journal of Catalysis, Apr. 1, 2013, vol. 300, pp. 37-46.
Yang et al., "Conversion of biomass into 5-hydroxymethylfurfural using solid acid catalyst". Bioresource Technology, Feb. 1, 2011 , vol. 102(3), pp. 3424-3429.
Patel et al., "Metal(IV) phosphates as solid acid catalysts for selective cyclodehydration of 1,n-diols". Green Chem., May 25, 2001 , vol. 3(3), pp. 143-145.
(Continued)

*Primary Examiner* — Timothy R Rozof
(74) *Attorney, Agent, or Firm* — Hill & Schumacher

(57) ABSTRACT

Disclosed is a cost-effective process for catalytic conversion of simple $C_6$-based sugars (such as glucose and fructose) and industrial-grade sugar syrups derived from starch (such as different grades of High Fructose Corn Syrup) and cellulosic biomass to 5-HydroxyMethylFurfural (5-HMF) in a continuous-flow tubular reactor in bi-phasic media using inexpensive heterogeneous solid catalysts. Commercial and synthesized heterogeneous solid catalysts were used and their activities in terms of sugar conversion and HMF selectivity and yield were compared. Continuous dehydration of fructose, glucose and industrial-grade sugar syrups derived from corn and wood to HMF was achieved and the stability of selected catalysts and feasibility of catalyst recycling and regeneration were demonstrated. The performance of the catalysts and reactor system were examined under different operating conditions including reaction temperature, feeding flow rate, initial feedstock concentration, catalyst loading, presence of extracting organic solvent and phase transfer catalyst and aqueous to organic phase ratio. At the best operating conditions, HMF yield attained 60%, 45% and 53%, from dehydration of fructose, glucose and HFCS-90, respectively.

33 Claims, 8 Drawing Sheets

(56) References Cited

OTHER PUBLICATIONS

Zhu et al., "Green Synthesis of Ni—Nb oxide Catalysts for Low-Temperature Oxidative Dehydrogenation of Ethane". ChemSusChem, Apr. 13, 2015, vol. 8(7), pp. 1254-1263.
Rao et al., "Simple and green route for preparation of tin phosphate catalysts by solid-state grinding for dehydration of glucose to 5-hydroxymethylfurfural (HMF)". RSC Advances, Oct. 17, 2017, vol. 7(76), pp. 48501-48511.
McNeff, C. V.; Nowlan, D. T.; McNeff, L. C.; Yan, B.; Fedie, R. L. Continuous Production of 5-Hydroxymethylfurfural from Simple and Complex Carbohydrates. Appl. Catal. A Gen. 2010, 384 (1-2), 65-69.
Brasholz, M.; von Känel, K.; Hornung, C. H.; Saubern, S.; Tsanaktsidis, J. Highly Efficient Dehydration of Carbohydrates to 5-(Chloromethyl) Furfural (CMF), 5-(Hydroxymethyl) Furfural (HMF) and Levulinic Acid by Biphasic Continuous Flow Processing. Green Chem. 2011, 13 (5), 1114-1117.
Carlini, C.; Giuttari, M.; Maria Raspolli Galletti, A.; Sbrana, G.; Armaroli, T.; Busca, G. Selective Saccharides Dehydration to 5-Hydroxymethyl-2-Furaldehyde by Heterogeneous Niobium Catalysts. Appl. Catal. A Gen. 1999, 183(2), 295-302.
International Search Report for the parent PCT application PCT/CA2017/050792, dated Feb. 7, 2018.

* cited by examiner

BI-PHASIC CONTINUOUS-FLOW TUBULAR REACTOR AND HETEROGENEOUS CATALYSTS PREPARATION METHOD FOR PRODUCTION OF 5-HYDROXYMETHYL FURFURAL

FIELD

The present disclosure relates to a method or process for cost-effective production of 5-hydroxymethyl furfural (5-HMF), which is a versatile intermediate or platform chemical and precursor for liquid bio-fuels and high-value biomass-based chemicals and polymeric materials at a high yield, from simple sugars and sugar syrups derived from starch or cellulosic biomass in a bi-phasic continuous-flow reactor using inexpensive heterogeneous catalysts.

BACKGROUND

Development of economically viable processes for production of renewable fuels and materials has become one of the major challenges nowadays for academia and industries due to the environmental and sustainability concerns associated with the use of the depleting fossil resources. [1,2] Biomass has attracted intensive attentions and more researchers have focused on using biomass as a renewable and sustainable feedstock due to its globally abundance, eco-friendly and carbon-neutral nature. [3-6] Biomass is a promising feedstock for not only sustainable production of bio-fuels, but also a wide variety of chemicals and materials with properties similar to, or even better than those derived from petroleum. [4]

Glucose is one of the main building blocks of biomass, particularly cellulose and starch. It can be biologically converted to bio-ethanol by fermentation (via removing $CO_2$) in industrial scale; however, this biological process is not efficient with regards to energy and carbon utilization efficiency. In addition, ethanol is characterized with low energy density, high volatility and tendency to absorb moisture from the air. [7] Therefore, many other processes are under development to efficiently convert the abundant bio-resources into higher energy content bio-fuels and chemicals, among which catalytic dehydration of carbohydrates to furan derivatives as intermediates for bulk production of bio-fuels and bio-based chemicals has attracted lots of interests due to its high reaction rate and better carbon efficiency. [8,9]

Recently, a great amount of research effort has been devoted toward the synthesis and production of 5-hydroxymethyl-2-furaldehyde or 5-hydroxymethyl furfural (5-HMF, referred to as "HMF" hereafter). [10] HMF was identified as one of the top 10 most valuable platform chemicals by the US Department of Energy as it is an important precursor and versatile intermediate that can be further converted into a variety of high-value bio-products including liquid bio-fuels and bio-based chemicals. [11-13] For instance, HMF can be converted to 2,5-dimethylfuran (DMF), a promising bio-fuel with a higher energy density and boiling point and lower volatility than bio-ethanol. [3] It can also be catalytically oxidized to 2,5-furandicarboxylic acid (FDCA), a green substitute for terephthalic acid (TPA) to produce polyethylene furanoate (PEF), a bio-substitute for polyethylene terephthalate (PET). [12,13]

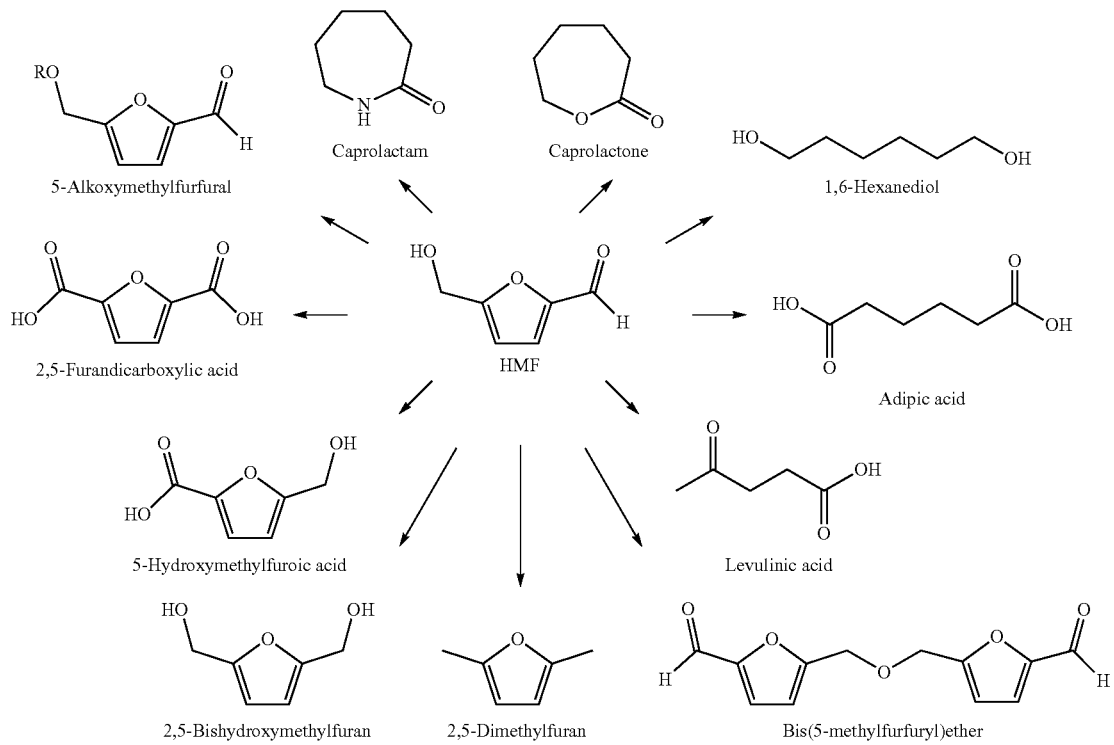

HMF as a Platform for Production of Biomass-Based Fuels and Chemicals, Reprinted with Permission from Ref [11] Copyright (2013) American Chemical Society Synthesis of HMF was first reported in 1895 by Dull et al. by heating inulin in an oxalic acid solution, and contemporaneously Kiermayer suggested a similar process for HMF synthesis using sugar cane. [11,14] In recent years, considerable efforts have been made on the transformation of carbohydrates into HMF. [8,9,13,15-21] HMF is mainly synthesized through the dehydration of $C_6$ monosaccharides (e.g., glucose and fructose) by losing three molecules of water. With glucose precursor, the reaction pathway consists of two consecutive reactions; i.e., isomerization of glucose to fructose and dehydration of fructose to HMF. [22,23] It has also been reported that the first reaction (isomerization) can be catalyzed by base (or Lewis acid) catalysts, while the second reaction (dehydration) can be catalyzed by acid (Brønsted acid) catalysts and this poses an interesting challenge in synthesis of HMF from glucose. [5,24,25]

A Reaction Scheme for Conversion of Glucose to HMF and Potential Side Reactions and by-Products, Reprinted from Ref. [5] Copyright (2009) the Royal Society of Chemistry Although HMF, its synthesis processes and broad applications have been known for many years and a great amount of research has been conducted and reported for HMF synthesis so far, the cost-effective commercial and industrial production of HMF has not been fully developed and realized yet to obtain furan type intermediate compounds in a large scale for the bulk production of bio-fuels and bio-based chemicals. This is due to some major barriers/challenges such as the difficulty of achieving a highly

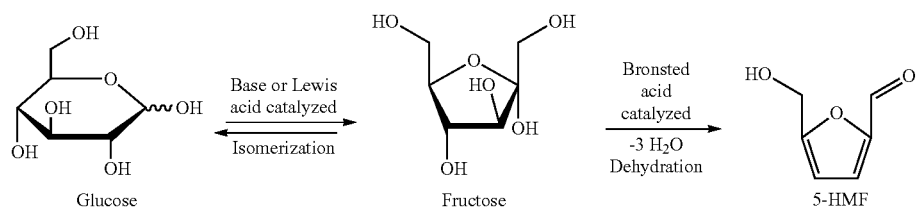

Two-step reaction pathways for catalytic conversion of glucose to HMF, reprinted from Ref. [5] Copyright (2009) The Royal Society of Chemistry and Ref. [25] Copyright (2015) Elsevier An important issue in production of HMF from dehydration of sugars with many existing processes is the low selectivity due to various side-reactions, in particular at elevated temperatures and in the presence of water, resulting in undesirable by-products such as levulinic and formic acids (through rehydration of HMF) as well as oligomeric humins (through condensation/self-polymerization of the feedstock, intermediates and product). [5,26]

selective process with a high yield of final product, and cost-effective method for product isolation as well as the feasibility of operating the process in a continuous-flow reactor that is desirable for large industrial scale production. That is why in the recent publications HMF has been named as a "Sleeping Giant".

So far, the only commercialized process for bulk production of HMF has been recently announced by AVA Biochem in Muttenz, Switzerland at its Biochem-1 facility. It was also announced that the Biochem-1 process, in its first phase, would produce up to 20 tons HMF per year. However, details about the AVA Biochem process (such as reactor

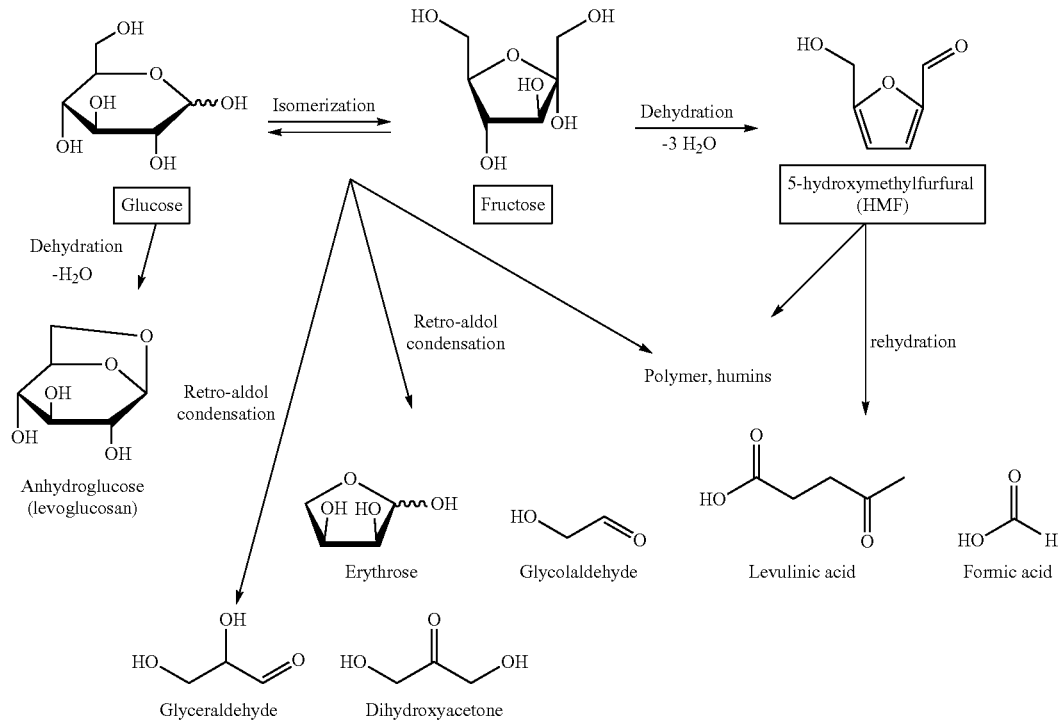

types, reaction medium, types of catalysts, yield and selectivity of HMF, etc.) have not been released in any public sources and therefore the inventors are unable to compare this the process of the present disclosure with the AVA Biochem process. In contrast, there have been a large number of lab-scale studies reported by far, in which a high HMF yield could be obtained with some high-cost processes (e.g., using high boiling point organic solvents such as DMSO, expensive media and catalysts such as ionic liquids, or operating at a high temperature, with costly separation processes or expensive equipment, etc.), while some low-cost processes developed by far produced HMF at relatively lower yields. It is thus highly desirable to develop cost-effective processes using inexpensive catalysts and reaction media, without sacrificing the product yield and selectivity.

The other issue for the existing HMF synthesis processes reported (mostly in a batch reactor) is their difficulty in upscaling. Generally, for industrial scale production, a continuous-flow process using heterogeneous catalyst is preferable for the ease of catalyst separation and reuse and effluent discharge. However, there is very limited research on HMF synthesis in continuous-flow reactors using heterogeneous catalysts. Technology advancements in reactor design and catalyst development are thus needed to achieve a high HMF selectivity and yield at a lower cost.

Another issue for consideration is preparation of active and selective heterogeneous solid catalysts through simple and inexpensive methods. Generally, solid heterogeneous catalysts were prepared through different methods including various wet-chemical processes such as co-precipitation, sol-gel processes, aqueous impregnation, reverse microemulsion technique and hydrothermal synthesis as well as some dry-chemical processes such as chemical vapor deposition and flame combustion techniques. In particular, heterogeneous metal phosphate catalysts are most often prepared through either conventional hydrothermal reaction or precipitation method. Despite the advantages of these methods of preparation, it must be noted that there are certain limitations associated with these methods such as relatively low yield, time consuming, and delicate pH/temperature control. In addition, the final product is contaminated with foreign elements and vast amount of environmental waste (e.g., salts from hydrolysis and wash water) is produced.

SUMMARY

The present disclosure addresses the abovementioned challenges by developing a novel and cost-effective continuous-flow process for production of HMF from simple sugars and sugar syrups with high selectivity and isolated yield in a bi-phasic (aqueous/organic) media using novel inexpensive heterogeneous solid catalysts prepared by a simple and green method through solid-solid grinding. Therefore, this novel technology advances the state-of-the-art of HMF production technology and has potential for bulk production of HMF in a large industrial scale.

More particularly, the present disclosure provides a novel and cost-effective process and technology for catalytic conversion of simple $C_6$-based sugars (particularly glucose and fructose) and industrial-grade sugar syrups derived from starch (such as different grades of High Fructose Corn Syrup) and cellulosic biomass to 5-HydroxyMethylFurfural (5-HMF) in a novel continuous-flow tubular reactor in bi-phasic media using novel inexpensive heterogeneous solid catalysts. Commercial and synthesized heterogeneous solid catalysts were used for the catalytic experiments and their activities in terms of sugar conversion and HMF selectivity and yield were compared. Continuous dehydration of fructose, glucose and industrial-grade sugar syrups derived from corn and wood to HMF was realized and the stability of some selected catalysts and feasibility of catalyst recycling and regeneration were demonstrated. The performance of the catalysts and reactor system were examined under different experimental and operating conditions including reaction temperature, feeding flow rate, initial feedstock concentration, catalyst loading, presence of extracting organic solvent and phase transfer catalyst and aqueous to organic phase ratio. At the best operating conditions, HMF yield attained 60%, 45% and 53%, from dehydration of fructose, glucose and HFCS-90, respectively.

Thus, in an embodiment there is provided a method for production of 5-hydroxymethyl furfural (5-HMF) from feedstock containing any one or combination of simple $C_6$-based sugars, industrial-grade sugar syrups and sugars derived from starch and/or cellulosic biomass, comprising:

continuously flowing a bi-phasic reaction medium including water, an organic solvent and the feedstock through an elongate tubular reactor having located therein a packed-bed column of heterogeneous solid catalyst containing any one or combination of Brønsted acid sites and Lewis acid sites, the packed-bed column extending along a preselected length of the said elongate tubular reactor, the packed-bed column of heterogeneous solid catalyst having first and second opposed ends located within the tubular reactor;

heating the elongate tubular reactor to a preselected temperature suitable for inducing reaction between a particular feedstock and a particular heterogenous solid catalyst;

monitoring temperatures of the first and second opposed ends of the packed-bed column and controlling and maintaining the temperature of the elongate tubular reactor such that the temperatures of the first and second opposed ends are within about 10° C. of each other;

operating the elongate tubular reactor at a pressure sufficiently high to prevent boiling of the water and the organic solvent at the preselected temperature such that the feedstock undergoes reaction to form 5-hydroxymethyl furfural in aqueous phase; and continuously and in-situ extracting the produced 5-hydroxymethyl furfural (HMF) from the aqueous phase to the organic phase/solvent as soon as produced while flowing through the tubular reactor.

The heterogeneous solid catalyst may be any one or combination of a metal phosphate, a metal oxide modified with an acid group and a heteropoly acid.

The metal phosphate may be any one of a phosphate of Nb, Sn, Ti, V, Cr, Zr, Al, Ga, Fe, Hf, and Ta.

The present disclosure also provides a reactor system for production of 5-hydroxymethyl furfural (5-HMF) from feedstock containing any one or combination of simple $C_6$-based sugars, industrial-grade sugar syrups and sugars derived from starch and/or cellulosic biomass, comprising:

an elongate bi-phasic continuous-flow tubular reactor having located therein a packed-bed column of heterogeneous solid catalyst containing any one or combination of Brønsted acid sites and Lewis acid sites, said packed-bed column extending along a preselected length of said elongate tubular reactor, said packed-bed column of heterogeneous solid catalyst having first and second opposed ends located within the tubular reactor;

temperature sensors positioned to sense the temperature at each of said opposed ends of said packed-bed column of heterogeneous solid catalyst;

a heat conducting element enveloping the said elongate tubular reactor, a heat generator surface inside a column heater attached to said heat conductor envelope, a temperature controller coupled to said column heater for controlling an maintaining a preselected temperature in said elongate tubular reactor;

a feedstock container and a first liquid pump for pumping aqueous liquid from said feedstock container;

an extracting solvent container and a second liquid pump for pumping extracting organic solvent from said extracting solvent container;

the first and second pumps being in flow communication with a reactor input passageway for flowing a bi-phasic mixture of aqueous feedstock and extracting organic solvent through said elongate tubular reactor and said packed-bed column of heterogeneous solid catalyst located therein;

a back-pressure regulator valve for regulating and controlling an internal pressure of the continuous-flow reactor, a pressure gauge for measuring the internal pressure; and an output conduit leading from an output port on said elongate tubular reactor to a product container, and an in-line filter located on said output conduit to filter the bi-phasic liquid product of the reaction.

The heterogeneous solid catalyst may be any one or combination of a metal phosphate, a metal oxide modified with an acid group and a heteropoly acid.

The metal phosphate may be a phosphate of any one of Nb, Sn, Ti, V, Cr, Zr, Al, Ga, Fe, Hf, and Ta.

The metal phosphate may be any one of anhydrous and hydrated niobium phosphate ($NbOPO_4$), wherein, and anhydrous and hydrated tin phosphate ($Sn(HPO_4)_2$).

The metal oxide may be any one of $TiO_2$, $ZrO_2$, $Nb_2O_5$, $Al_2O_3$, $SnO_2$, $HfO_2$, and $Ta_2O_5$.

The heteropoly acid may be any one of $H_3PW_{12}O_{40}$, $H_4SiW_{12}O_{40}$ and $H_3PMo_{12}O_{40}$.

The present disclosure also provides a method of producing a heterogeneous catalyst, comprising:

solid-solid grinding of any one of powders of anhydrous or hydrated tin phosphate ($Sn(HPO_4)_2$), anhydrous or hydrated zirconium phosphate, anhydrous or hydrated hafnium phosphate, anhydrous or hydrated chromium phosphate, anhydrous or hydrated tantalum phosphate and anhydrous or hydrated niobium phosphate together with sodium dihydrogen phosphate dihydrate ($NaH_2PO_4 \cdot 2H_2O$) powders at about room temperature to form a colourless thick viscous liquid followed by oven drying at about 60 to about 150° C. to produce a powder composition, washing the powder composition with water to remove sodium and chloride ions, followed by vacuum drying at about 60 to about 150° C., calcining the as-synthesized SnP catalyst at about 200 to 400° C. for about 2 to 8 hours.

A further understanding of the functional and advantageous aspects of the present disclosure can be realized by reference to the following detailed description and drawings.

BRIEF DESCRIPTION OF THE DRAWINGS

Embodiments will now be described, by way of example only, with reference to the drawings, in which.

DETAILED DESCRIPTION

Figure 1:
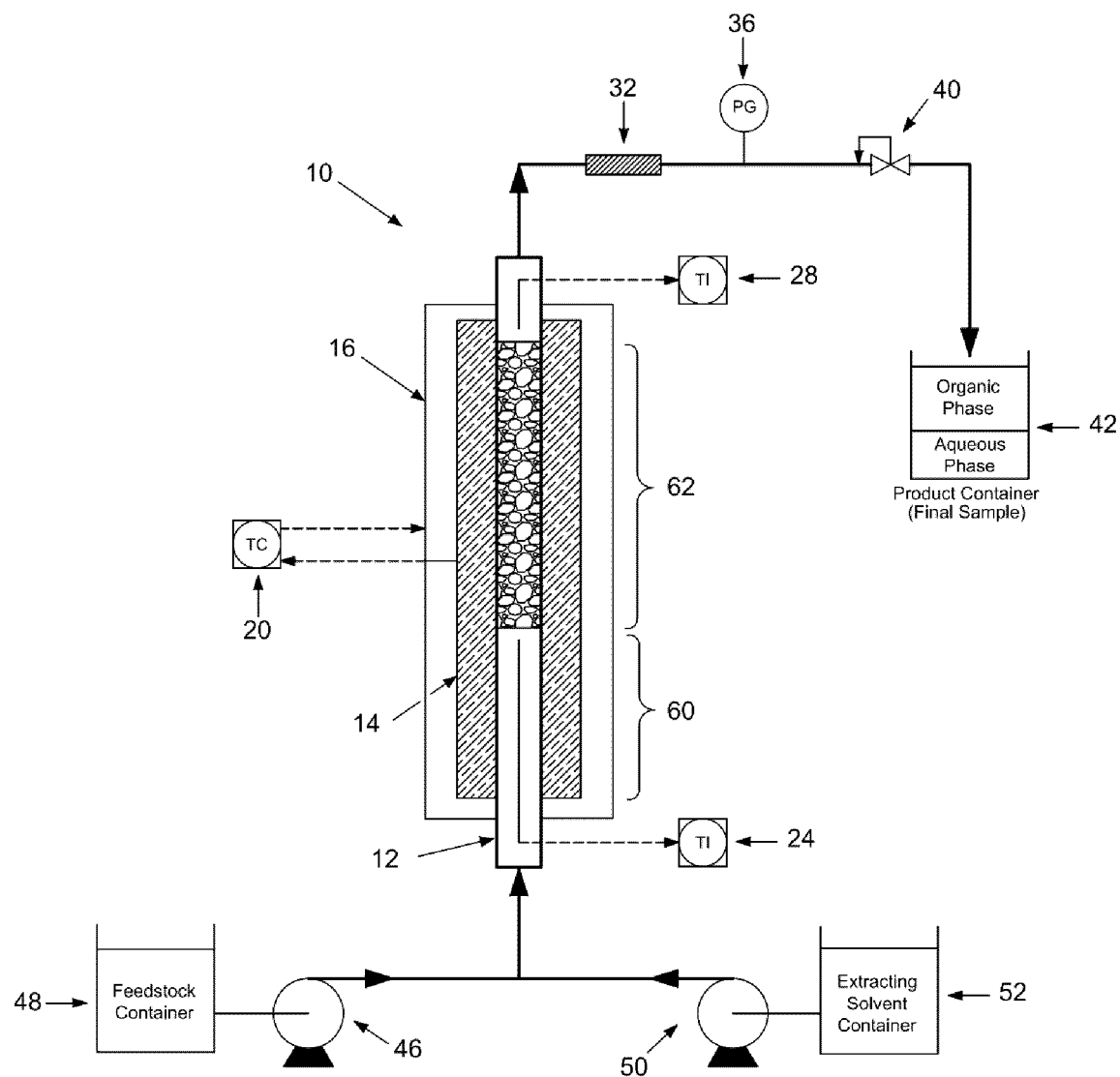
FIG. 1 shows a schematic diagram of a bi-phasic continuous-flow tubular reactor system used for implementing the present method disclosed herein.

Various embodiments and aspects of the disclosure will be described with reference to details discussed below. The following description and drawings are illustrative of the disclosure and are not to be construed as limiting the disclosure. The Figures are not to scale. Numerous specific details are described to provide a thorough understanding of various embodiments of the present disclosure. However, in certain instances, well-known or conventional details are not described in order to provide a concise discussion of embodiments of the present disclosure.

As used herein, the terms, "comprises" and "comprising" are to be construed as being inclusive and open ended, and not exclusive. Specifically, when used in the specification and claims, the terms, "comprises" and "comprising" and variations thereof mean the specified features, steps or components are included. These terms are not to be interpreted to exclude the presence of other features, steps or components.

As used herein, the terms "Examples" or "exemplary" means "serving as an example, instance, or illustration," and should not be construed as preferred or advantageous over other configurations disclosed herein.

As used herein, the terms "about" or "approximately" are meant to cover variations that may exist in the upper and lower limits of the ranges of values, such as variations in properties, parameters, and dimensions. In one non-limiting example, the terms "about" and "approximately" mean plus or minus 10 percent or less.

Unless defined otherwise, all technical and scientific terms used herein are intended to have the same meaning as commonly understood to one of ordinary skill in the art.

As used herein, when referring to a bi-phasic reaction medium, it typically contains water and an immiscible organic solvent (or a miscible organic solvent by adding a mineral salt to the aqueous phase to make it immiscible with water) to continuously and in-situ extract the formed HMF from aqueous phase. The extracting organic solvent preferably has a low boiling point and it could be a cyclic ether (such as, but not limited to tetrahydrofuran, 2-methyltetrahydrofuran and 1,4-dioxane), a non-polar organic solvent, for example straight, branched and cyclic alkanes (such as, but not limited to n-pentane, cyclopentane, n-hexane, cyclohexane, etc.), ketones (such as, but not limited to methyl isobutyl ketone, methyl propyl ketone, acetone, etc.), alcohols (such as, but not limited to n-butanol, 2-butanol, and pentanol) and aromatic organic solvents (such as, but not limited to benzene, toluene and substitute benzene solvents) or even a mixture of different organic solvents. However, the most preferred organic solvent which was used in this process is methyl isobutyl ketone (MIBK).

As used herein, when referring to feedstock, this means a feedstock containing any one or combination of $C_6$-based sugars, industrial-grade sugar syrups and sugars derived from starch and/or cellulosic biomass. More particularly it means any kind of sugar solution/syrup containing mono, di, tri or polysaccharides. Monosaccharides could be aldohexose (such as, but not limited to glucose, mannose, galactose) or ketohexose (such as, but not limited to fructose) while disaccharides (such as, but not limited to sucrose, lactose, cellobiose and maltose) and trisaccharides (such as, but not limited to, raffinose, maltotriose, isomaltotriose) could also be used. Polysaccharides (such as, but not limited to starch, cellulose and hemicellulose) consist of a long chain of monosaccharides linked by glycosidic bonds which give the constituent monosaccharides or oligosaccharides by acid hydrolysis could also be used. Preferred feedstocks used in the process disclosed herein are fructose, glucose or a sugar syrup derived from starch or cellulosic biomass (such as, but not limited to, different grades of high fructose corn syrup, glucose corn syrup and wood hydrolysis sugar) which contains glucose and/or fructose.

As used herein, when referring to catalyst, this refers to heterogeneous solid catalysts preferably containing both Brønsted and Lewis acid sites. The solid acid catalysts are most preferably metal (such as, but not limited to Nb, Sn, Ti, V, Cr, Zr, Al, Ga, Fe, Hf, Ta) phosphates. Metal oxides (such as, but not limited to $TiO_2$, $ZrO_2$, $Nb_2O_5$, $Al_2O_3$, $SnO_2$, $HfO_2$, and $Ta_2O_5$) modified with acid groups (such as, but not limited to $PO_4^{-3}$, $SO_4^{-2}$) and heteropoly acids (such as, but not limited to, $H_3PW_{12}O_{40}$, $H_4SiW_{12}O_{40}$ and $H_3PMo_{12}O_{40}$) may also be used as solid acid catalysts.

Broadly, the present disclosure provides a method for production of 5-hydroxymethyl furfural (5-HMF) from feedstock containing any one or combination of $C_6$-based sugars, industrial-grade sugar syrups and sugars derived from starch and/or cellulosic biomass. The method involves continuously flowing a bi-phasic reaction medium comprised of water, an organic solvent and the feedstock through an elongate tubular reactor having located therein a packed-bed column of heterogeneous solid catalyst.

In some cases, a heterogeneous solid catalyst with only Brønsted acid sites may be required, while in other cases a heterogeneous solid catalyst with only Lewis acid sites may be required and in other cases a heterogeneous solid catalyst with both Lewis acid sites and Brønsted acid sites may be required. Thus, depending on the starting material, the heterogeneous solid catalyst may contain any one or combination of Brønsted acid sites and Lewis acid sites. For example, for isomerization of glucose to fructose Lewis acid sites (or basic catalysts) are required while for dehydration of fructose to HMF Brønsted acid sites are needed, therefore for direct conversion of glucose to HMF the heterogenous solid catalyst should have both Brønsted acid sites and Lewis acid sites. The packed-bed column of the catalyst extends along a preselected length of the elongate tubular reactor. The method includes heating the elongate tubular reactor to a preselected temperature suitable for the reaction.

The temperatures of the opposed ends of the packed-bed of catalyst column are monitored and the temperature of the elongate tubular reactor is controlled and maintained such that the temperatures of the opposed ends are within about 10° C. of each other, while a more preferred temperature difference is approximately 5° C.

The temperature at which the reactor is operated will depend on the type of feedstock and the particular organic solvent(s) which are used. While many studies were performed, and very good results obtained at 150° C., it will be appreciated that the reactor can be operated at different temperatures depending on the organic solvent and the starting material. The reaction temperature can be determined and optimized by design of experiments or screening tests, which are standard and well understood in the art.

The reactor is operated at a pressure sufficiently high to prevent boiling of the water and the particular organic solvent at the preselected temperature such that the feedstock undergoes reaction to form 5-hydroxymethyl furfural (HMF) in the aqueous phase and is continuously extracted in-situ to the organic solvent/phase as soon as produced while flowing through the tubular reactor.

Materials

D-(+)-glucose (>99.5%), D-(−)-fructose (>99%) and 5-hydroxymethylfurfural (99%), for preparing HPLC standard solutions, as well as Amberlyst 15, Amberlyst 36, triethylamine (TEA), sodium chloride (NaCl), Tin chloride pentahydrate ($SnCl_4.5H_2O$), sodium dihydrogen phosphate dihydrate ($NaH_2PO_4.2H_2O$), titanium iso-propoxide, aluminium iso-propoxide, zirconium (IV) n-propoxide (70 wt % in 1-propanol) and zirconium oxychloride octahydrate ($ZrOCl_2.8H_2O$) were purchased from Sigma-Aldrich, Canada. High Fructose Corn Syrups (HFCS) of different grades (HFCS-42, HFCS-55 and HFCS-90) and Glucose Corn Syrup (GCS) samples were supplied by a local food industry plant and their characteristics are listed in Table 1. The TMP-Bio Sugar was supplied by FPInnovations, Canada, which contains 320 g/L glucose and 100 g/L xylose. Niobium pentoxide ($Nb_2O_5$) hydrate also called as niobic acid and niobium phosphate ($NbOPO_4$) hydrate were supplied by CBMM (Companhia Brasileira de Metalurgia e Mineraçã). Calcium phosphate dibasic ($CaHPO_4$) and chromic phosphate ($CrPO_4$) were purchased from MP Biomedicals Company. HPLC grade water and acetonitrile, for preparing the mobile phase for HPLC analysis, as well as methyl isobutyl ketone (MIBK), phosphoric acid (85%), nitric acid (70%) and sulfuric acid (93%) were purchased from Caledon Laboratory Chemicals, and used as received.

TABLE 1

Characteristics of the HFCS and GCS samples

| Sample | Dry Substance (wt %) | Fructose (wt % db [a]) | Glucose (wt % db [a]) | Higher Saccharides (wt % db [a]) |
|---|---|---|---|---|
| HFCS-42 | 70.5-71.5 | 42.0 | 52.0 | 6.0 |
| HFCS-55 | 76.8-77.4 | 55.0 | 40.0 | 5.0 |
| HFCS-90 | 77.4 | 92.1 | 5.6 | 2.3 |
| GCS | 48.0 | 3.2 | 91.4 | 5.4 |

[a] Dry basis

Catalysts Preparation

In order to be able to use powder solid catalysts in a plug flow reactor as a catalytic packed-bed, pelletization of the powder catalysts was performed. Commercial catalysts, Niobium phosphate ($NbOPO_4$) hydrate (referred to hereinafter as NbP for simplification), niobic acid ($Nb_2O_5$ hydrate, hereinafter referred to as NbA), chromic phosphate ($CrPO_4$, hereinafter referred to as CrP) and calcium phosphate dibasic ($CaHPO_4$, hereinafter referred to as CaP) powders were humidified overnight and then were pressed in an evacuable pellet die by using hydraulic press (Specac Atlas) at 15 tonnes/cm$^2$ of pressure to create pellets. The pellets were then crushed using a Wiley Mill and sieved and particles of sizes between 420-840 μm (Mesh No. 40 to Mesh No. 20) were collected and used for the experiments after thoroughly washing with deionized water and drying at 80° C. Amberlyst 15 (hereinafter referred to as Amb. 15) and Amberlyst 36 beads (thereafter named as Amb. 36) were used as received.

Tin phosphate ($Sn(HPO_4)_2$) hydrate (referred to hereinafter as SnP for simplification) catalyst with P/Sn molar ratio of 1.0 was prepared by a simple and green approach via solid-solid grinding of tin chloride pentahydrate ($SnCl_4.5H_2O$) and sodium dihydrogen phosphate dihydrate ($NaH_2PO_4.2H_2O$) powders at about room temperature in a mortar and pestle to form a colourless thick viscous liquid followed by oven drying at 100° C. overnight (but could be carried out in the range from about 60° C. to about 150° C.). The obtained white solid was the washed with deionized water to remove sodium and chloride ions, followed by vacuum drying at 60° C. overnight (but could be carried out in the range 60° C. to about 150° C.). The as-synthesized SnP catalyst was calcined at 300° C. for 4 hours (but could be carried out at a temperature in a range from about 200 to about 400° C. for a period of time from about 2 to 8 hours.

Similar procedure was followed for the preparation of zirconium phosphate (thereafter named as ZrP) catalyst by using zirconium oxychloride octahydrate ($ZrOCl_2.8H_2O$) as zirconium precursor. Both SnP and ZrP catalyst were then pelletized into pellets followed by crushing and sieving to obtain particles of 425-850 μm in the same method as NbP.

The above-noted method producing heterogeneous catalysts using solid-solid catalysts may be used to prepare other metal phosphate catalysts. Specifically, heterogeneous catalysts may be prepared by solid-solid grinding of any one of the powders of anhydrous or hydrated tin phosphate ($Sn(HPO_4)_2$), anhydrous or hydrated zirconium phosphate, anhydrous or hydrated hafnium phosphate, anhydrous or hydrated chromium phosphate, anhydrous or hydrated tantalum phosphate and anhydrous or hydrated niobium phosphate together with sodium dihydrogen phosphate dihydrate ($NaH_2PO_4.2H_2O$) powders at about room temperature to form a colourless thick viscous liquid. This liquid is the oven dried at about 60 to about 150° C. to produce a powder composition followed by washing the powder composition with water to remove sodium and chloride ions, followed by vacuum drying at about 60 to about 150° C., calcining the as-synthesized catalyst at about 200 to 400° C. for about 2 to 8 hours.

Phosphated titania (15 mol % P, hereinafter named as 15P/$TiO_2$) was prepared through a simple single-step sol-gel technique. In a typical synthesis, 70% (v/v) nitric acid (7.22 mL) was added into a stirred solution of titanium iso-propoxide (51.5 mL) in iso-propanol (27 mL) followed by dropwise addition of 85% phosphoric acid (3.937 g). Then, a solution of iso-propanol (48 mL) in deionized water (11.6 mL) was dropwise added to the former solution to form a gel. After resting for 2 hours to settle, the solvent was evaporated and the gel was dried in open air at 90° C. for 4 hours. The obtained solid material was calcined in air at 300° C. for 4 hours. Similarly, 15P/$ZrO_2$, 15P/$Al_2O_3$ and 15$SO_4$/$Al_2O_3$ catalysts were prepared by the same procedure as described above where zirconium (IV) n-propoxide and aluminum iso-propoxide were taken as precursors for $ZrO_2$ and $Al_2O_3$. In the case of 15$SO_4$/$Al_2O_3$ catalyst, concentrated $H_2SO_4$ was used for sulfonation of aluminum alkoxide instead of $H_3PO_4$. In all catalysts preparation, metal/water molar ratio was fixed at 0.3. All these catalysts were then pelletized into pellets followed by crushing and sieving to obtain particles of 425-850 μm in the same method as NbP.

Reactor Setup

The catalytic conversion of simple sugars and industrial-grade sugar syrups (such as HFCS) to HMF was performed in a novel bi-phasic continuous-flow tubular reactor system developed in this invention, as schematically shown generally at 10 in FIG. 1. The tubular reactor system 10 was used for testing different heterogeneous solid catalysts as a fixed-bed within the tubular flow reactor 12 for conversion of simple sugars (e.g., glucose or fructose) and industrial-grade sugar syrups to HMF. A solution of pure sugar or industrial-grade sugar syrup derived from starch/cellulose in aqueous medium was used as the feedstock and methyl isobutyl ketone (MIBK) was utilized as the organic extracting solvent. MIBK continuously extracts the produced HMF from the aqueous medium in-situ inside the tubular reactor 12, in order to enhance the HMF selectivity and yield by suppressing the side reactions of HMF in water. Sodium chloride (NaCl) was also added to the aqueous phase as the phase transfer catalyst (PTC) to enhance the partition coefficient of HMF towards the organic phase (via the salting-out effect).

The reactor system 10 includes a vertical tubular reactor (SS-316 ½" or ⅝" tubes-30 cm long) 12 seamlessly fitted inside a custom-manufactured bipartite solid aluminum column envelope 14 to form a heat conductor envelope which is adhered to a heat generator surface inside a column heater 16 (Eppendorf CH-30). The heating mechanism of the reactor system 10 is novel as the heat is provided by heat conduction from the bipartite solid aluminum column envelope 14 along the tubular reactor 12, thereby giving constant and uniform temperature distribution in the fixed-bed of the catalyst 62. Herewith, aluminum is used as the heat conduction material for the column envelope 14 because of its superior thermal conductivity to facilitate transferring the generated heat from the heat generator surface to the tubular reactor 12. In the column heater 16, the temperature of the heat generator surface is controlled using a temperature controller 20 (Eppendorf TC-50).

In the experiments, appropriate amount of heterogeneous solid catalyst (particle size between 420-840 μm) was preloaded and supported inside the tubular reactor 12 as a packed-bed 62 between two quartz wool plugs at the upper ⅔ length of the reactor (20 cm, reaction zone) 62 while lower ⅓ length of the reactor (10 cm, pre-heating zone) 60 remains empty to pre-heat the flowing bi-phasic media to the predetermined reaction temperature before entering the reaction zone (catalyst bed) 62.

Two high pressure liquid metering pumps 46 and 50 (Eldex Optos Series 2SMP) provide independent and adjustable flow rates of aqueous phase (solution of sugar feedstock and NaCl salt in deionized water) contained in feedstock container 48 (pump 46) and organic phase (pure MIBK extracting solvent) contained in extracting solvent container 52 (pump 50) and then two phases are mixed in a tee union connected to the bottom of the tubular reactor 12 to provide a uniform upward rising flow of bi-phasic media through the tubular reactor 12. The temperature of the flowing bi-phasic media inside the tubular reactor 12 is also monitored using two thermocouples (Omega ⅛" K-type) located just before and after the reaction zone (catalyst bed) 62 and connected to digital temperature meters 24 (for lower thermocouple) and 28 (for upper thermocouple). The pressure of the reactor system 10 is adjusted and controlled using a back-pressure regulator valve 40 (Swagelok KBP Series) located on the exit line of the reactor 10 and the pressure of the system is also indicated on a pressure gauge 36 located upstream of back-pressure regulator valve 40.

In a typical run, after preloading a specific amount (typically 14 g in some best runs) of the heterogeneous solid catalyst particles into the reaction zone 62 of the tubular reactor 12 within the aluminum column envelope 14 inside the column heater 16, the aqueous feedstock solution (typically containing 200 mg/ml sugar and 200 mg/ml NaCl) was pumped into the tubular reactor 12 from feedstock container 48 using the dedicated feeding pump 46 at a specific flow rate (typically 0.25 ml/min). Once the tubular reactor 12 was filled up with the feedstock solution and it came out from the exit line to the product container 42, the extracting organic solvent (typically MIBK) was pumped from extracting solvent container 52 using the dedicated solvent pump 50 at a specific flow rate (typically 1.25 ml/min) to the tubular reactor 12 concurrently. Then the pressure inside the reactor system 10 was increased to the desired pressure (typically 10 bars) using the back-pressure regulator valve 40 to avoid boiling of the water and extracting organic solvent at high reaction temperatures and the formation of vapor bubbles within the reactor system. The tubular reactor 12 was then heated up to the desired temperature (typically 150° C. in some best runs) after insulating the column heater 16 and the tubular reactor 12. After the tubular reactor 12 reached a stable temperature at the set-point and the steady state condition was achieved (depending on the feeding flow rate), samples were taken in every hour and the concentrations of sugar feedstock and HMF in each phase were analyzed by High Performance Liquid Chromatography (HPLC) in order to determine the sugar conversion as well as HMF selectivity and yield.

The time on stream (TOS) for all the experiments was 8 hours except for some experiments that continued for 20-24 hours to examine the catalyst stability, when interestingly no soluble by-products or any other intermediates were detectable by HPLC analysis.

Weight hourly space velocity (WHSV) was used as an indicator of the reactant retention/residence time within the catalyst bed, which is defined as follows, correlating the feedstock concentration, feeding flow rate and mass of catalyst loaded in the test:

$$WHSV\ (hr^{-1}) = \frac{\text{Feed Concentration} \times \text{Feeding Flow Rate}}{\text{Mass of Catalyst}} \quad (1)$$

The particle size of the catalysts ($d_p$) and internal diameter of the tubular reactor (D) were in a suitable range ($6 < D/d_p < 30$) to avoid wall effects, high pressure drop and channeling flow of the fluid inside the fixed-bed of the catalyst.

Most experiments were performed in duplicates, in order to ensure the repeatability of the results and to minimize the experimental errors (<5%). For simplification, in figures and tables of the results, mean values of the data along with the relative errors are presented.

Product Analysis

Each phase (organic and aqueous) of the product samples collected from the experiments was separately analyzed using an HPLC (Waters 2690 Separation Module) equipped with both RI detector (Waters 410 Differential Refractometer) with internal detector temperature of 35° C. and UV detector (Waters 484 Tunable Absorbance Detector) set at 284 nm to determine the amount of feedstock (sugar) consumed and the amount of product (HMF) produced, respectively. Waters XBridge Amide column (3.5 μm, 4.6× 250 mm) maintained at 35° C. was used and the mobile phase was 75/25 acetonitrile/water (v/v) with 0.2 v % triethylamine (TEA) at the flow rate of 0.6 ml/min. The results for all experiments were analyzed by external calibration curves generated for fructose, glucose and HMF separately using standard solutions of fructose, glucose and HMF with known concentrations (6 levels). The results are reported in terms of conversion, selectivity and yield, which are defined and calculated as follows:

$$\text{Sugar Conversion (\%)} = \frac{\text{Moles of sugar converted}}{\text{Initial moles of sugar}} \times 100\% = \quad (2)$$

$$\frac{[(C_{Sugar}^{aqu,F} \times Q^{aqu}) - (C_{Sugar}^{aqu,P} \times Q^{aqu})]/M_{Sugar}}{(C_{Sugar}^{aqu,F} \times Q^{aqu})/M_{Sugar}} \times 100\% =$$

$$\frac{C_{Sugar}^{aqu,F} - C_{Sugar}^{aqu,P}}{C_{Sugar}^{aqu,F}} \times 100\%$$

$$\text{HMF Selectivity (\%)} = \quad (3)$$

$$\frac{\text{Total moles of HMF produced in both phases}}{\text{Moles of sugar converted}} \times 100\% =$$

$$\frac{[(C_{HMF}^{aqu,P} \times Q^{aqu}) + (C_{HMF}^{org,P} \times Q^{org})]/M_{HMF}}{[(C_{Sugar}^{aqu,F} \times Q^{aqu}) - (C_{Sugar}^{aqu,P} \times Q^{aqu})]/M_{Sugar}} \times 100\% =$$

$$\frac{\left[C_{HMF}^{aqu,P} + \left(C_{HMF}^{org,P} \times \frac{Q^{org}}{Q^{aqu}}\right)\right]/M_{HMF}}{(C_{Sugar}^{aqu,F} - C_{Sugar}^{aqu,P})/M_{Sugar}} \times 100\%$$

-continued

HMF Yield in Aqueous Phase (%) = (4)

$$\frac{\text{Moles of HMF produced in both phase}}{\text{Initial moles of sugar}} \times 100\% =$$

$$\frac{(C_{HMF}^{aqu,P} \times Q^{aqu})/M_{HMF}}{(C_{Sugar}^{aqu,F} \times Q^{aqu})/M_{Sugar}} \times 100\% = \frac{C_{HMF}^{aqu,P}/M_{HMF}}{C_{Sugar}^{aqu,F}/M_{Sugar}} \times 100\%$$

HMF Yield in Organic Phase (%) = (5)

$$\frac{\text{Moles of HMF produced in organic phase}}{\text{Initial moles of sugar}} \times 100\% =$$

$$\frac{(C_{HMF}^{aqu,P} \times Q^{org})/M_{HMF}}{(C_{Sugar}^{aqu,F} \times Q^{aqu})/M_{Sugar}} \times 100\% =$$

$$\frac{\left(C_{HMF}^{org,P} \times \frac{Q^{org}}{Q^{aqu}}\right)/M_{HMF}}{C_{Sugar}^{aqu,F}/M_{Sugar}} \times 100\%$$

Total HMF Yield (%) = (6)

$$\frac{\text{Total moles of HMF produced in both phases}}{\text{Initial moles of sugar}} \times 100\% =$$

$$\frac{[(C_{HMF}^{aqu,P} \times Q^{aqu}) + (C_{HMF}^{org,P} \times Q^{org})]/M_{HMF}}{(C_{Sugar}^{aqu,F} \times Q^{aqu})/M_{Sugar}} \times 100\% =$$

$$\frac{\left[C_{HMF}^{aqu,P} + \left(C_{HMF}^{org,P} \times \frac{Q^{org}}{Q^{aqu}}\right)\right]/M_{HMF}}{C_{Sugar}^{aqu,F}/M_{Sugar}} \times 100\%$$

where,
$C_{Sugar}^{aqu,P}$ is mass concentration of sugar in the aqueous feedstock solution (mg/ml),
$C_{Sugar}^{aqu,P}$ is mass concentration of sugar in the aqueous phase of product sample (mg/ml),
$C_{HMF}^{aqu,P}$ is mass concentration of HMF in the aqueous phase of product sample (mg/ml),
$C_{Sugar}^{aqu,P}$ mass concentration of HMF in the organic phase of product sample (mg/ml),
$Q^{aqu}$ is volumetric flow rate of the aqueous feedstock solution (ml/min),
$Q^{org}$ is volumetric flow rate of the extracting organic solvent (ml/min),
$M_{Sugar}$ is molar mass of sugar (=180.16 g/mol for glucose and fructose),
$M_{HMF}$ is molar mass of HMF (=126.11 g/mol).

The present method will now be illustrated with the following non-limiting Examples.

Example 1 (Fructose to HMF)

Initially, the catalytic dehydration of fructose to HMF using heterogeneous solid acid catalysts in the bi-phasic continuous-flow tubular reactor system was investigated. Different heterogeneous solid acid catalysts including niobium phosphate (NbP), niobic acid (NbA), Amberlyst 15 (Amb. 15) and Amberlyst 36 (Amb. 36) were comprehensively characterized and their activities for dehydration of fructose to 5-hydroxymethylfurfural (5-HMF) were tested in the bi-phasic continuous-flow tubular reactor. The effects of different reaction parameters such as initial fructose concentration, reaction temperature, feeding flow rate, addition of a phase transfer catalyst (NaCl), presence or absence of an organic phase, and aqueous to organic phase ratio were tested, in order to achieve higher HMF selectivity and yield. Some major and key results are summarized as follows.

It was demonstrated that HMF selectivity and yield from fructose were significantly higher in the bi-phasic system than in a single aqueous phase.

With the bi-phasic media, increasing the extracting organic (O) solvent to aqueous (A) phase ratio (or decreasing NO) and employing a phase transfer catalyst (NaCl) had positive effects on fructose dehydration reaction, leading to significantly increased HMF selectivity and yield by suppressing side reactions (e.g., polymerization and rehydration of HMF) and formation of humins.

NbP and Amb. 36 catalysts were the most active catalysts among all catalysts tested for dehydration of fructose to HMF.

At lower reaction temperatures (110 and 130° C.), NbP catalyst showed considerably higher activities than other catalysts tested, attributed to its larger total number of acid sites, higher Brønsted to Lewis acid sites ratio (B/L) and larger BET surface area.

Figure 2A:
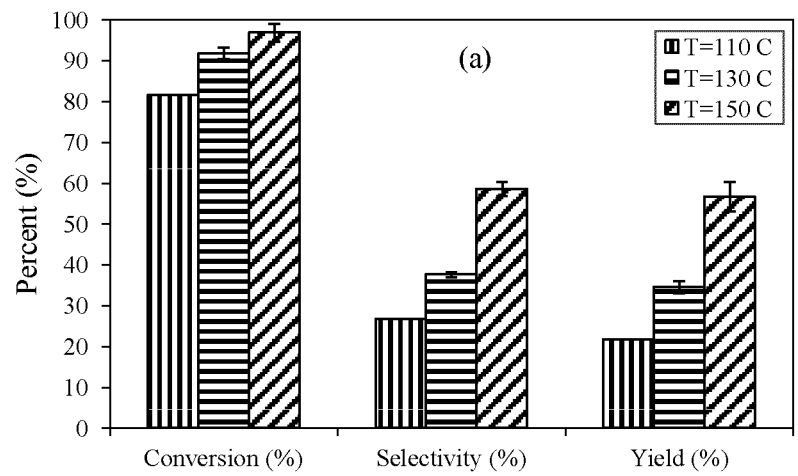
FIG. 2(a) shows the effects of different reaction temperatures on dehydration of fructose to HMF over NbP catalyst in terms of conversion, selectivity and yield with a feeding flow rate of 0.25 ml/min (WHSV=0.428 h$^{-1}$), initial fructose concentration of 400 mg/ml (~40 wt %), NaCl concentration of 200 mg/ml, A/O=1:5 (v/v).
Figure 2B:
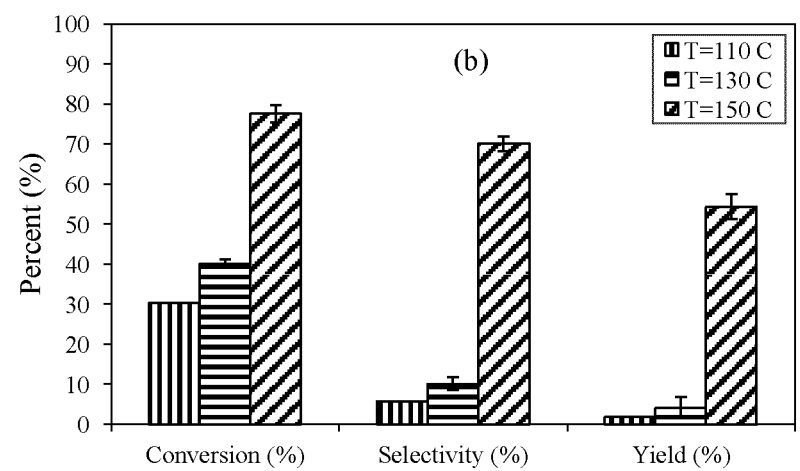
FIG. 2(b) shows the effects of different reaction temperatures on dehydration of fructose to HMF over Amb. 36 catalyst in terms of conversion, selectivity and yield with a feeding flow rate of 0.25 ml/min (WHSV=0.428 h$^{-1}$), initial fructose concentration of 400 mg/ml (~40 wt %), NaCl concentration of 200 mg/ml, A/O=1:5 (v/v).

The activity of the catalysts improved with increasing temperature and this enhancement was surprisingly drastic for Amb. 36. With Amb. 36 while increasing the temperature from 110° C. to 150° C., the fructose conversion increased from 30.3% to 77.5%, and HMF selectivity jumped from <6% to 70.1% (FIGS. 2(a) and 2(b)).

Figure 3:
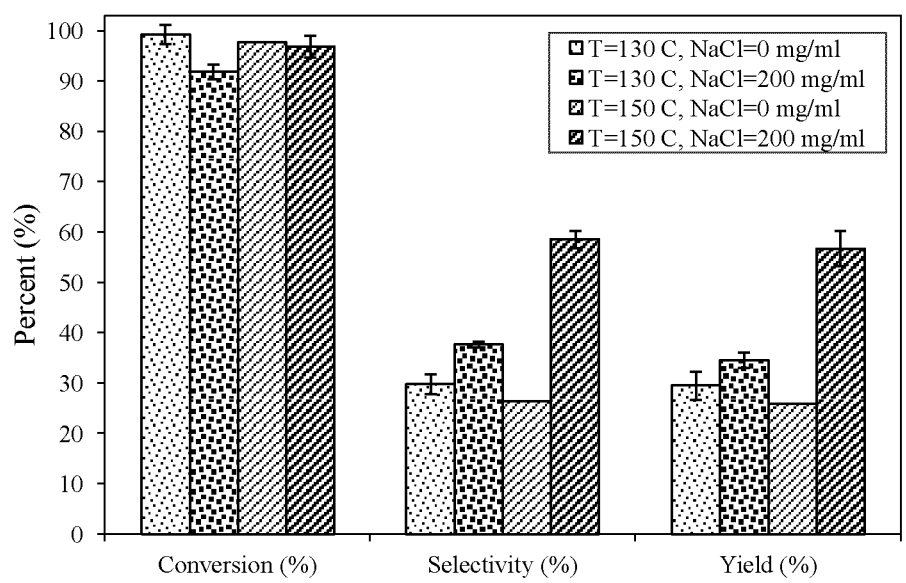
FIG. 3 shows the effects of NaCl on dehydration of fructose to HMF over NbP catalyst in terms of conversion, selectivity and yield at 130° C. and 150° C. with a feeding flow rate of 0.25 ml/min (WHSV=0.428 h$^{-1}$), initial fructose concentration of 400 mg/ml (~40 wt %), A/O=1:5 (v/v).

Fructose conversion with and without phase transfer catalyst (NaCl) remained almost constant (>90%) in the presence of NbP catalyst. However, the HMF selectivity and yield both increased when NaCl was added to the feedstock solution and this effect became more evident at a higher temperature (150° C.). Such results thus suggest that the presence of the inorganic salt in the reaction system contributed to the in-situ extraction of HMF from the aqueous phase to the organic phase, which would then suppress the side reactions and hence increasing the HMF selectivity and yield (FIG. 3). With NbP catalyst and 200 mg/mL NaCl at 150° C., fructose dehydration attained ~100% sugar conversion, and the highest selectivity and yield of 58.5% and 56.7%, respectively.

The best operating conditions for catalytic dehydration of fructose to HMF in the bi-phasic continuous-flow reactor was found to be: temperature of 150° C., aqueous feed flow rate of 0.25 ml/min, organic solvent (MIBK) flow rate of 1.25 ml/min (NO ration of 1:5 (v/v)), fructose and NaCl concentrations in the aqueous feedstock solution of 200 to 400 mg/ml and 200 mg/ml, respectively. Table 2 summarizes the activity of the NbP and Amb. 36 catalysts at the best operating conditions for production of HMF from fructose in the bi-phasic continuous-flow reactor. With these catalysts at the above best operating conditions, fructose dehydration in the bi-phasic continuous-flow tubular reactor produced HMF at both high selectivity (55-70%) and high yield (54-60%).

TABLE 2

Catalytic activity of NbP and Amb. 36 catalysts at the best operating conditions for production of HMF from fructose in the bi-phasic continuous-flow reactor

| | Catalyst Loading (g) | | | |
|---|---|---|---|---|
| | NbP | | Amb. 36 | |
| | 7 | 14 | 14 | 24 |
| | Fructose Concentration (mg/ml) | | | |
| | 400 [a] | 400 [b] | 400 [b] | 200 [c] |
| Conversion (%) | 98.9 ± 1.9 | 96.9 ± 2.2 | 77.5 ± 2.2 | 91.9 ± 0.8 |
| Selectivity (%) | 54.9 ± 3.1 | 58.5 ± 1.7 | 70.1 ± 1.8 | 64.8 ± 1.7 |
| Yield (%) | 54.3 ± 3.5 | 56.7 ± 3.5 | 54.3 ± 3.1 | 59.6 ± 1.9 |

[a] WHSV = 0.856 h$^{-1}$
[b] WHSV = 0.428 h$^{-1}$
[c] WHSV = 0.125 h$^{-1}$

The Amb. 36 catalyst showed a superb stability after 8 hours of time on stream (TOS), with even better selectivity and only a small decrease in fructose conversion and HMF yield, suggesting that this catalyst is relatively stable in operation and can be recycled and reused without losing much of its activity. After running the experiments for 8 hours of time on stream, the system was cooled down and washed by pumping distilled water through the tubular reactor 12 while the used catalysts were still packed inside the reaction zone 62. The reactor system 10 was then left overnight and it was again tested the next day with fresh feedstock and the used catalyst inside the reactor (without any further treatment/regeneration on the used catalyst) for another 8-hour TOS and the results are compared with those achieved with the fresh catalysts, as shown in Table 3, where it is clear that the used catalyst produced almost similar HMF yield 54.2%, compared with 59.6% with fresh catalyst.

TABLE 3

Performance of the fresh and used Amb. 36 catalyst at 150° C.[a]

|  | Fresh Catalyst | Used Catalyst |
|---|---|---|
| Conversion (%) | 91.9 ± 0.8 | 81.7 ± 2.2 |
| Selectivity (%) | 64.8 ± 1.7 | 66.3 ± 0.8 |
| Yield (%) | 59.6 ± 1.9 | 54.2 ± 2.5 |

[a] Feeding flow rate of 0.25 ml/min, NaCl concentration of 200 mg/ml, A/O = 1:5 (v/v), Catalyst dosage of 24 g, Initial fructose concentration of 200 mg/ml (WHSV = 0.125 h$^{-1}$)

The catalyst deactivation mechanisms were investigated by TGA analysis of the used NbP catalyst at different reaction temperatures, and the results evidenced that the deposition of insoluble humins on the surface of the catalyst particles is one of the main cause and mechanisms for catalyst deactivation.

Example 2 (Glucose to HMF)

The catalytic dehydration of glucose to HMF was tested in the bi-phasic continuous-flow tubular reactor system using different heterogeneous solid acid catalysts and the effects of different operating conditions such as aqueous to organic (NO) phase ratio, reaction temperature and feeding flow rate on the activity of some selected catalysts were examined.

Some major and key results are summarized as follows:
Comparing the results for the individual catalysts tested for dehydration of glucose to HMF (Table 4) shows that NbP (commercial catalyst) and SnP (self-developed and synthetized catalyst) are the most active catalysts with the highest HMF selectivity (38.8% and 39.1%, respectively) and yield (37.6% and 37.8%, respectively) and close to 100% glucose conversion at 150° C. (WHSV=0.214 h$^{-1}$ and A/O=1:5 (v/v)). The higher activity of NbP and SnP catalysts may be attributed to their high acidity (total number of acid sites), presence of both Lewis and Brønsted acid sites on the catalyst surface as well as large BET surface area.

TABLE 4

Performance of different solid catalysts in glucose dehydration at 150° C.[a]

| Catalyst | Conversion (%) | Selectivity (%) | HMF Yield (%) | | |
|---|---|---|---|---|---|
| | | | Aqueous Phase | Organic Phase | Total |
| NbP | 96.9 ± 1.5 | 38.8 ± 0.5 | 3.8 ± 0.5 | 33.8 ± 1.2 | 37.6 ± 1.7 |
| SnP | 96.6 | 39.1 | 3.9 | 33.9 | 37.8 |
| 15P/TiO$_2$ | 99.3 | 31.9 | 3.4 | 28.2 | 31.6 |
| ZrP | 53.3 | 44.8 | 2.3 | 21.0 | 23.3 |
| 15P/ZrO$_2$ | 48.7 | 30.6 | 1.5 | 13.4 | 14.9 |
| 15P/Al$_2$O$_3$ | 99.4 | 12.7 | 1.4 | 11.2 | 12.6 |
| 15SO$_4$/Al$_2$O$_3$ | 98.4 | 16.7 | 1.7 | 14.8 | 16.4 |
| CrP | 51.3 ± 0.8 | 24.0 ± 0.1 | 1.2 ± 0.1 | 11.1 ± 0.4 | 12.3 ± 0.5 |
| CaP | 19.6 | 36.1 | 0.7 | 6.4 | 7.1 |
| Amb. 36 | 32.0 | 21.8 | 0.7 | 6.3 | 7.0 |

[a] Initial glucose concentration of 200 mg/ml (~20 wt %), NaCl concentration of 200 mg/ml, Feeding flow rate of 0.25 ml/min, MIBK flow rate of 1.25 ml/min (A/O = 1:5 (v/v)), Catalyst loading of 14 g, (WHSV = 0.214 h$^{-1}$)

The Amb. 36 catalyst exhibited the lowest activity in terms of HMF yield (6.9%) which can be attributed to the absence of Lewis acid sites on the surface of Amberlyst catalysts while the Lewis acid sites are believed to be responsible for catalyzing the isomerization reaction of glucose to fructose as the first step of the reaction pathway of glucose conversion to HMF.

A lower A/O (by increasing the extracting organic solvent flow rate) was found to be in favor of HMF formation as expected. In the presence of NbP catalyst, the aqueous feedstock solution flow rate in all the tests was kept constant at 0.25 ml/min (WHSV=0.214 hr$^{-1}$) while the flow rate of MIBK was adjusted at 0.50, 1.25 and 2.50 ml/min (corresponding to NO of 1:2, 1:5 and 1:10 (v/v), respectively). The results show an increasing trend in HMF selectivity and yield when the MIBK flow rate was increased from 0.50 to 1.25 and 2.50 ml/min indicating that side reactions were suppressed in the presence of a higher amount of MIBK as the extracting organic solvent. The same increasing trend in HMF selectivity and yield was observed using SnP catalyst when the MIBK flow rate was increased from 1.25 to 2.50 ml/min (corresponding to NO of 1:5 and 1:10 (v/v), respectively). However, in the experiment with NbP catalyst when the aqueous and organic phases flow rates were decreased to 0.10 and 1.00, respectively (keeping the same A/O of 1:10 (v/v)), a drop in HMF selectivity and yield was observed. This likely resulted from too long retention time of the aqueous feedstock phase (a much lower WHSV of 0.086 hr$^{-1}$) as well as the organic phase inside the reactor due to the lower flow rates which could promote the side reactions to degrade the HMF or self-polymerize the feedstock, reaction intermediates and product to humins, leading to a reduction in HMF selectivity and yield (Table 5).

TABLE 5

Effects of aqueous to organic phase ratio (A/O) on
the catalytic activity of NbP and SnP at 150° C.[a]

| Catalyst | Flow rates (ml/min) | | | Conversion (%) | Selectivity (%) | HMF Yield (%) | | |
|---|---|---|---|---|---|---|---|---|
| | Aqueous Phase | Organic Phase | A/O Ratio | | | Aqueous Phase | Organic Phase | Total |
| NbP | 0.25 | 0.50 | 1:2 | 96.5 ± 0.9 | 29.7 ± 2.1 | 6.3 ± 1.5 | 22.4 ± 0.7 | 28.7 ± 2.2 |
| NbP | 0.25 | 1.25 | 1:5 | 96.9 ± 1.5 | 38.8 ± 0.5 | 3.8 ± 0.5 | 33.8 ± 1.2 | 37.6 ± 1.7 |
| NbP | 0.25 | 2.50 | 1:10 | 99.4 ± 0.2 | 45.2 ± 1.1 | 2.3 ± 0.3 | 42.6 ± 0.7 | 45.0 ± 1.0 |
| NbP | 0.10 | 1.00 | 1:10 | 100 | 17.5 | 1.7 | 15.8 | 17.5 |
| SnP | 0.25 | 1.25 | 1:5 | 96.6 | 39.1 | 3.9 | 33.9 | 37.8 |
| SnP | 0.25 | 2.50 | 1:10 | 96.4 | 47.3 | 2.3 | 43.3 | 45.6 |

[a] Initial glucose concentration of 200 mg/ml (~20 wt %), NaCl concentration of 200 mg/ml A very high HMF yield of 45% was achieved from glucose dehydration in the bi-phasic continuous-flow tubular reactor with 14 g of either NbP or SnP catalysts at 150° C. and the NO of 1:10 (MIBK flow rate of 2.5 ml/min and feeding flow rate of 0.25 ml/min) using 200 mg/ml aqueous glucose solution containing 200 mg/ml NaCl as a phase transfer catalyst.

Figure 4A:
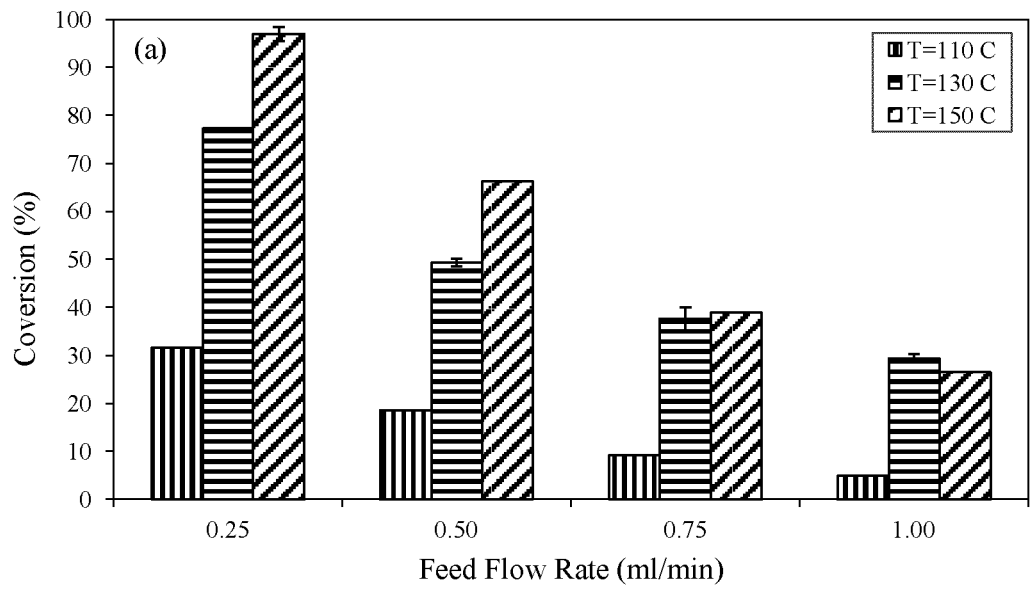
FIG. 4(a) shows the effects of different reaction temperatures and feeding flow rates on glucose conversion over NbP catalyst with initial glucose concentration of 200 mg/ml, NaCl concentration of 200 mg/ml, A/O=1:5 (v/v).
Figure 4B:
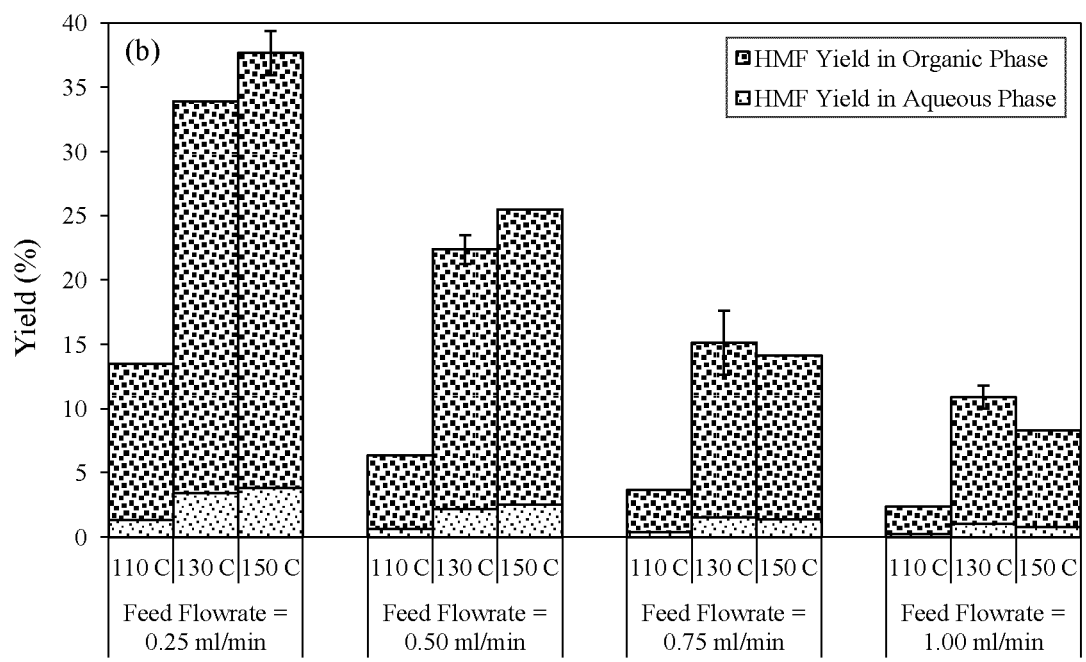
FIG. 4(b) shows the effects of different reaction temperatures and feeding flow rates on HMF yield over NbP catalyst with initial glucose concentration of 200 mg/ml, NaCl concentration of 200 mg/ml, A/O=1:5 (v/v).

At a fixed temperature, increasing the feeding flow rate of aqueous phase from 0.25 to 0.50, 0.75 and 1.00 ml/min (corresponding to WHSV of 0.21, 0.43, 0.64 and 0.86 hr$^{-1}$, respectively; i.e., decreasing retention time of the substrate inside the reactor) results in lower glucose conversions and consequently lower HMF yields. On the other hand, at a constant feeding flow rate, increasing the reaction temperature showed a positive effect on the glucose conversion and HMF yield (FIGS. 4(a) and 4(b)).

Kinetics study of the overall glucose conversion reaction in the presence of NbP catalyst showed that a first-order reaction kinetics model adequately fits the experimental data for all three tested temperatures. The reaction rate constants (k) were determined as 0.06, 0.21 and 0.6 min$^{-1}$ at 110, 130 and 150° C., respectively, and the apparent activation energy ($E_a$) was calculated as 77 kJ/mol using Arrhenius Equation.

Figure 5A:
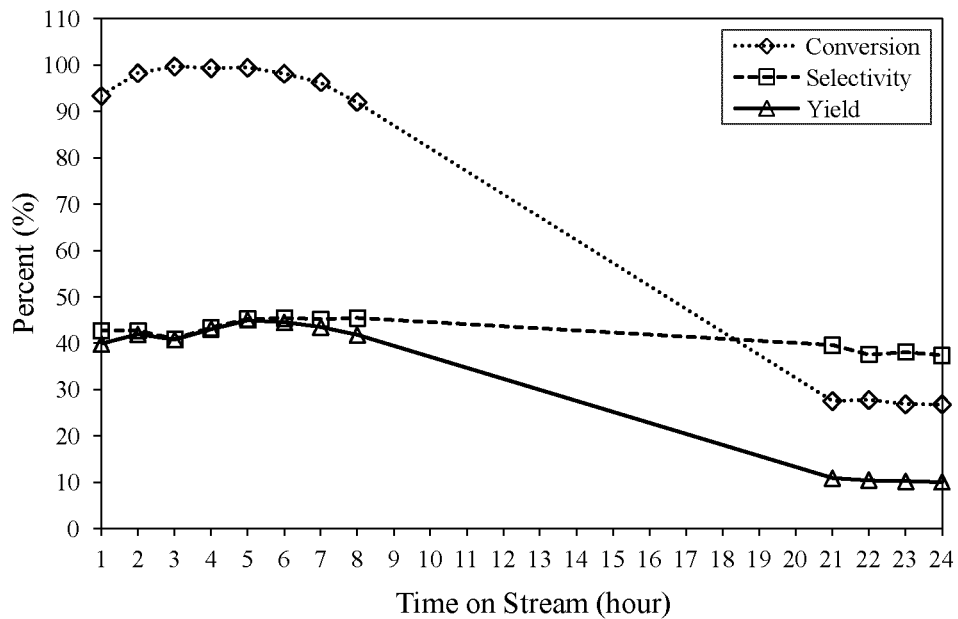
FIG. 5(a) shows the activity of NbP catalyst for conversion of glucose to HMF at 150° C. over the time on stream in terms of conversion, selectivity and yield with initial glucose concentration of 200 mg/ml, NaCl concentration of 200 mg/ml, feeding flow rate of 0.25 ml/min, MIBK flow rate of 2.5 ml/min, A/O=1:10 (v/v).
Figure 5B:
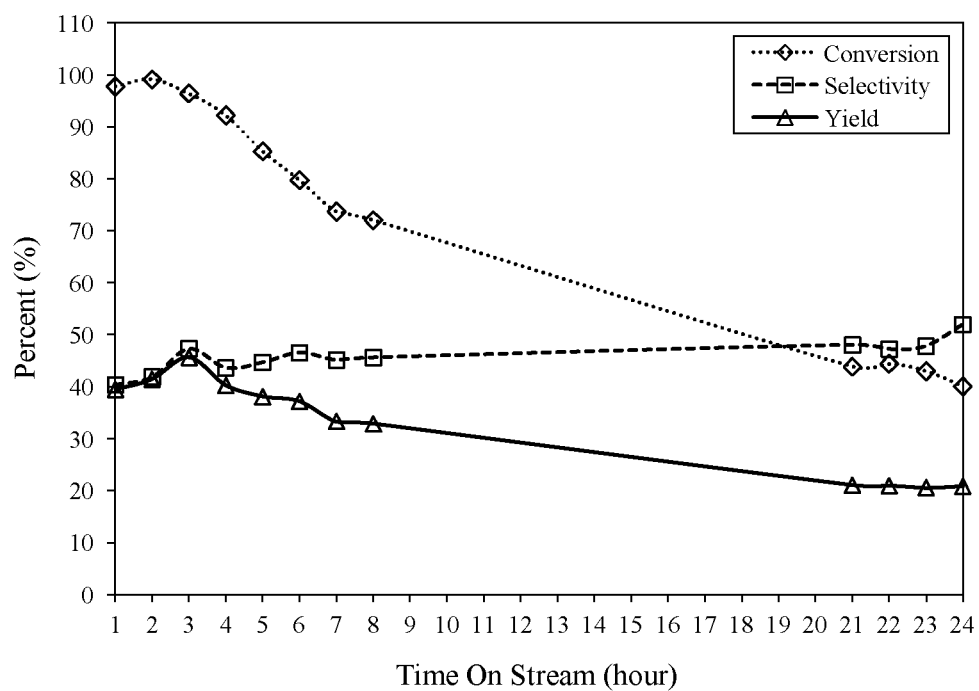
FIG. 5(b) shows the activity of SnP catalyst for conversion of glucose to HMF at 150° C. over the time on stream in terms of conversion, selectivity and yield with initial glucose concentration of 200 mg/ml, NaCl concentration of 200 mg/ml, feeding flow rate of 0.25 ml/min, MIBK flow rate of 2.5 ml/min, A/O=1:10 (v/v).

To study the stability of the catalysts with time, the experiments with NbP and SnP catalysts and A/O of 1:10 (feeding flow rate of 0.25 ml/min and MIBK flow rate of 2.5 ml/min) were performed and monitored continuously for 24-hour time on stream (TOS) and the results for the activities of the catalysts in terms of glucose conversion and HMF selectivity and yield are shown in FIG. 5(a) (for NbP catalyst) and FIG. 5(b) (for SnP catalyst). The activities of NbP and SnP catalysts were found to drop after 24-hour time on stream, suggesting deactivation of the catalysts which could be due to the formation of insoluble humins that deposited on the surface of the catalyst particles, while the NbP catalysts fairly maintained its activity in the first 8 hours of time on stream.

The regenerated SnP catalyst (after being used in a 24-hour experiment) by simply calcination in air (500° C. for 5 hours) showed a good activity, with almost the same selectivity, although at a lower glucose conversion and reduced HMF yield compared to the fresh catalyst at the same operating conditions (Table 6). This implied that the deposition of the insoluble humins on the surface of the catalyst particles is the main cause and mechanism of the catalyst deactivation, however the simple regeneration process (calcination in air) could recover a part of the acid sites on the catalyst surface.

TABLE 6

Comparison of activities for fresh SnP catalyst (at 3 hours TOS), fresh
SnP catalyst (after 24 hours TOS) and the simply regenerated SnP catalyst
(at 3 hours TOS) for conversion of glucose to HMF at 150° C.[a]

| SnP catalyst | Conversion (%) | Selectivity (%) | HMF Yield (%) | | |
|---|---|---|---|---|---|
| | | | Aqueous Phase | Organic Phase | Total |
| Fresh (at 3 hr TOS) | 96.4 | 47.3 | 2.3 | 43.3 | 45.6 |
| Fresh (after 24 hr TOS) | 40.1 | 52.0 | 1.0 | 19.9 | 20.9 |
| Regenerated (at 3 hr TOS) | 75.0 | 49.5 | 1.9 | 35.2 | 37.1 |

[a] Initial glucose concentration of 200 mg/ml (~20 wt %), NaCl concentration of 200 mg/ml, Feeding flow rate of 0.25 ml/min, MIBK flow rate of 2.50 ml/min, A/O of 1:10 (v/v), Catalyst loading of 14 g, (WHSV = 0.214 h$^{-1}$)

Figure 6A:
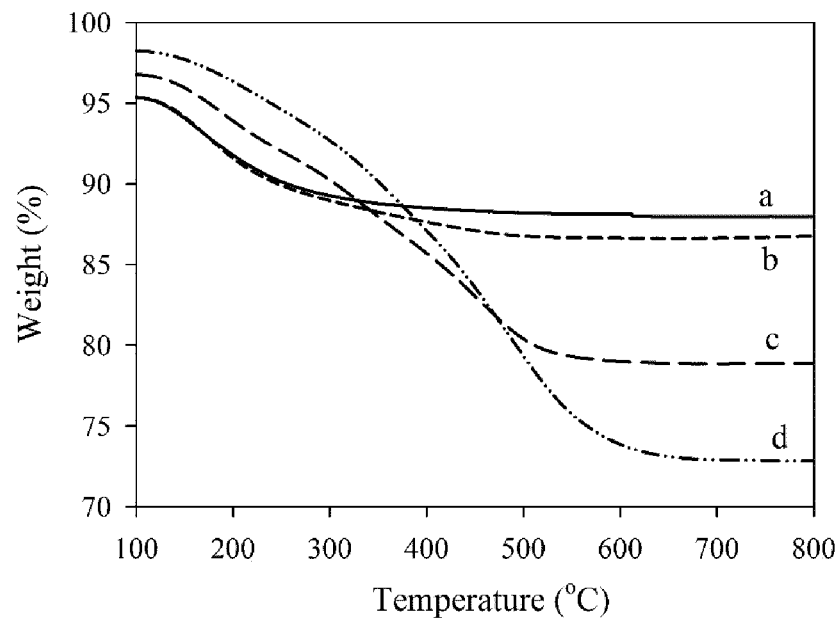
FIG. 6(a) shows the TGA graphs for the fresh NbP catalyst (a) and used NbP catalysts after experiments at 110° C. (b), 130° C. (c) and 150° C. (d).
Figure 6B:
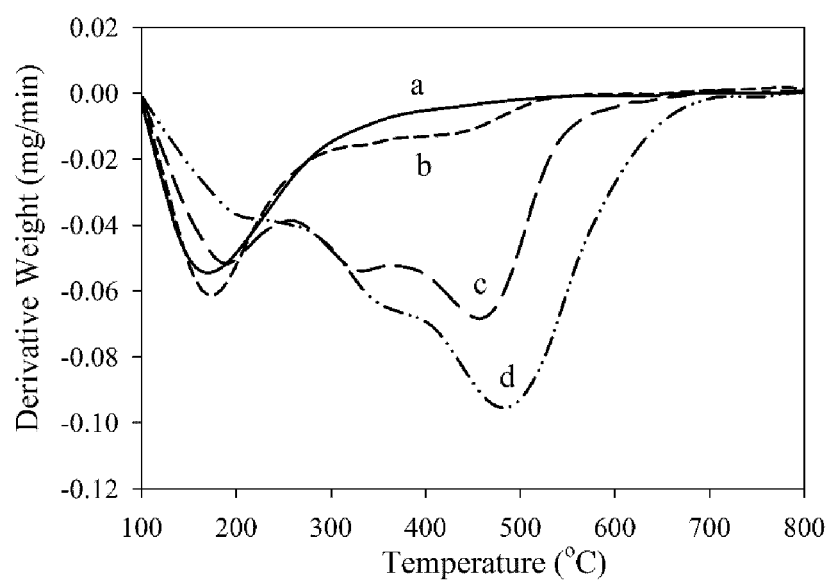
FIG. 6(b) shows the DTG graphs for the fresh NbP catalyst (a) and used NbP catalysts after experiments at 110° C. (b), 130° C. (c) and 150° C. (d).

Characterization of the used NbP catalyst by TGA/DTG and BET/PSD showed the deposition of the insoluble humins on the surface of the catalyst particles during the reaction as a function of reaction temperature, leading to catalysts deactivation (FIGS. 6(a) and 6(b) and Table 7).

TABLE 7

Textural properties of the fresh NbP catalyst and used NbP catalysts after
experiments at 110° C., 130° C. and 150° C.

| Catalyst | BET Surface Area (m$^2$/g) | Average Pore Diameter (nm) | Total Pore Volume (cm$^3$/g) |
|---|---|---|---|
| Fresh NbP | 246 | 5 | 0.31 |
| Used NbP at 110° C. | 160 | 6.2 | 0.26 |
| Used NbP at 130° C. | 118 | 5.3 | 0.16 |
| Used NbP at 150° C. | 24 | 4.3 | 0.03 |

Example 3 (Industrial-Grade Sugar Syrups to HMF)

This work demonstrated promise of using industrial-grade sugar syrups derived from corn and wood, i.e., high fructose corn syrup (HFCS), glucose corn syrup (GCS) and wood-based sugar (TMP-Bio Sugar), as cheaper and competitive feedstocks for bulk production of HMF using niobium phosphate (NbP) as a heterogeneous solid acid catalyst in a bi-phasic continuous-flow tubular reactor.

Some major and key results are summarized as follows.

Catalytic dehydration of High Fructose Corn Syrup (HFCS) of different grades and Glucose Corn Syrup (GCS) feedstocks in the presence of NbP catalyst resulted in high HMF yield and complete sugar conversion. The HMF selectivity and yield from these feedstocks varied according to their fructose content and the highest HMF yield of 53.1% was obtained from HFCS-90 (containing 90 wt % fructose) at 150° C., with feed concentration of 200 mg/ml (glucose and fructose) and aqueous to organic phase ratio of 1:5 (Table 8).

TABLE 8

HMF production from different industrial-grade sugar syrups derived from corn and wood in the presence of NbP catalyst at 150° C. [a]

| Feedstock | Conversion (%) | Selectivity (%) | HMF Yield (%) | | |
|---|---|---|---|---|---|
| | | | Aqueous Phase | Organic Phase | Total |
| HFCS-90 | 100 | 53.0 ± 2.2 | 4.8 ± 1.0 | 48.3 ± 0.2 | 53.0 ± 1.2 |
| HFCS-55 | 99.5 ± 0.1 | 50.3 ± 0.9 | 4.6 ± 0.7 | 45.5 ± 0.3 | 50.0 ± 0.8 |
| HFCS-42 | 98.7 ± 0.3 | 47.7 ± 1.4 | 4.4 ± 0.8 | 42.7 ± 0.2 | 47.1 ± 1.1 |
| GCS | 96.9 ± 0.8 | 40.4 ± 1.3 | 3.7 ± 0.5 | 35.4 ± 0.6 | 39.1 ± 1.1 |
| TMP-Bio Sugar | 62.8 ± 2.4 | 33.8 ± 1.1 | 2.3 ± 0.4 | 19.0 ± 1.8 | 21.3 ± 2.2 |

[a] Initial glucose + fructose concentration of 200 mg/ml (~20 wt %), NaCl concentration of 200 mg/ml, Feeding flow rate of 0.25 ml/min, MIBK flow rate of 1.25 ml/min, A/O of 1:5 (v/v), Catalyst loading of 14 g The TMP-Bio Sugar (wood-based sugar) and GCS feedstocks were mostly composed of glucose, so their HMF yields were much lower than those of HFCS feedstocks, being 21.3% and 39.1%, respectively. The lower glucose conversion and HMF yield from the TMP-Bio Sugar compared to GCS was likely due to the presence of impurities such as soluble polymers and oligomers produced from hydrolysis of cellulose, hemicellulose and lignin as well as xylose that is dehydrated to furfural.

Figure 7:
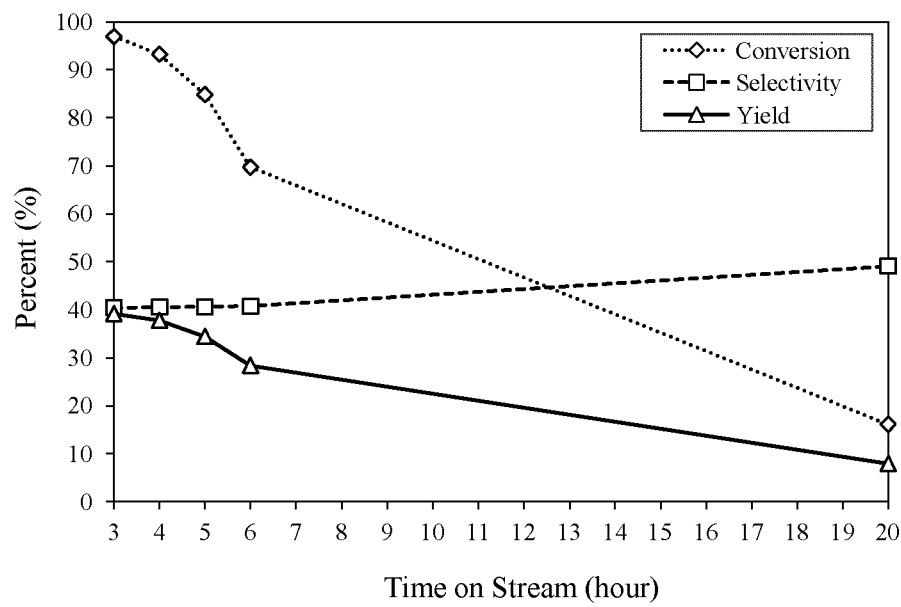
FIG. 7 shows the activity of NbP catalyst for conversion of GCS to HMF at 150° C. over the time on stream in terms of conversion, selectivity and yield with initial glucose+fructose concentration of 200 mg/ml, NaCl concentration of 200 mg/ml, feeding flow rate of 0.25 ml/min, MIBK flow rate of 1.25 ml/min, A/O of 1:5 (v/v).

The NbP catalyst after 20-hour time on stream for the GCS dehydration experiment resulted in a considerable drop in glucose conversion, and a substantial decrease in HMF yield, suggesting catalyst deactivation likely due to deposition of insoluble humins and coke on the surface of the catalyst particles (FIG. 7). However, the regenerated catalyst by in-situ calcination (600° C. for 4 hours) under air flow (100 ml/min) showed good activity, with almost the same selectivity, although at a lower glucose conversion and reduced HMF yield compared to the fresh catalyst (Table 9). This implied that the deposition of the insoluble humins on the surface of the catalyst particles is the main cause and mechanism for catalyst deactivation, however the simple in-situ regeneration process (calcination under air flow) could recover a part of the acid sites on the catalyst surface.

TABLE 9

Comparison of activities for fresh NbP catalyst (at 3 hr TOS), fresh NbP catalyst (after 20 hr TOS) and the simply regenerated NbP catalyst (at 3 hr TOS) for conversion of GCS to HMF at 150° C. [a]

| NbP catalyst | Conversion (%) | Selectivity (%) | HMF Yield (%) | | |
|---|---|---|---|---|---|
| | | | Aqueous Phase | Organic Phase | Total |
| Fresh (at 3 hr TOS) | 96.9 ± 0.8 | 40.4 ± 1.3 | 3.7 ± 0.5 | 35.4 ± 0.6 | 39.1 ± 1.1 |
| Fresh (after 20 hr TOS) | 16.1 | 49.0 | 0.7 | 7.2 | 7.9 |
| Regenerated (at 3 hr TOS) | 75.3 ± 2.0 | 36.7 ± 1.8 | 2.7 ± 1.2 | 25.0 ± 0.7 | 27.7 ± 1.9 |

[a] Initial feedstock (glucose) concentration of 200 mg/ml (~20 wt %), NaCl concentration of 200 mg/ml, Feeding flow rate of 0.25 ml/min, MIBK flow rate of 1.25 ml/min, A/O of 1:5 (v/v), Catalyst loading of 14 g, (WHSV = 0.214 h$^{-1}$)

Figure 8:
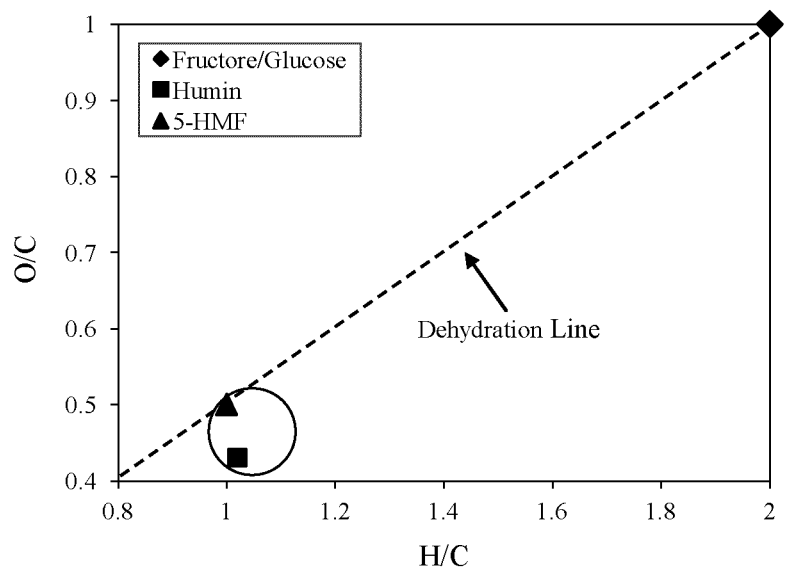
FIG. 8 shows a Van Krevelen diagram for insoluble humins by-product, glucose/fructose and HMF.
Figure 9:
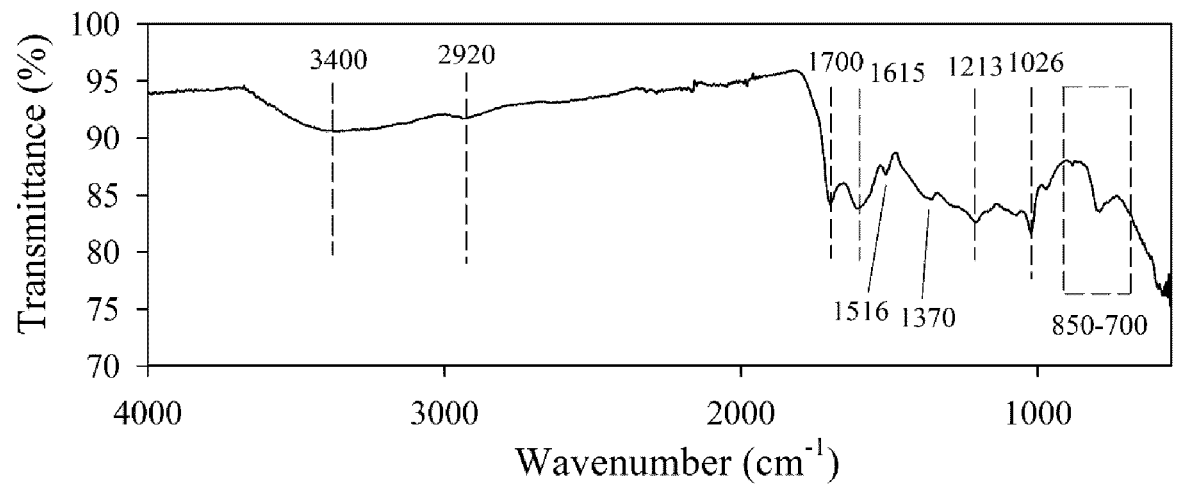
FIG. 9 shows an infrared Fourier transform (FT-IR) spectrum of the insoluble humins by-product.

Characterizations of the insoluble humin by-product collected in this work, using elemental analysis (CHNS) and Fourier transform infrared spectrometry (FT-IR) showed high aromaticity and presence of high degree of unsaturated compounds in the structure of humins (Table 10 and FIG. 8 and FIG. 9). It was further confirmed in this work that the insoluble humins had similar elemental composition and chemical structure (i.e., containing furan and unsaturated structure) to that of HMF, indicating that humins were produced from either dehydration of glucose/fructose or self-polymerization of HMF (without further dehydration).

TABLE 10

Elemental composition of the humins by-product compared with glucose/fructose and HMF

| Sample | Elemental Composition (wt %) | | | Molar Ratio | |
|---|---|---|---|---|---|
| | C | H | O[a] | H/C | O/C |
| Humin | 59.87 | 5.09 | 34.17 | 1.02 | 0.43 |
| Glucose/Fructose | 40.00 | 6.67 | 53.33 | 2 | 1 |
| HMF | 57.14 | 4.77 | 38.09 | 1 | 0.5 |

[a]By Difference

Figure 10:
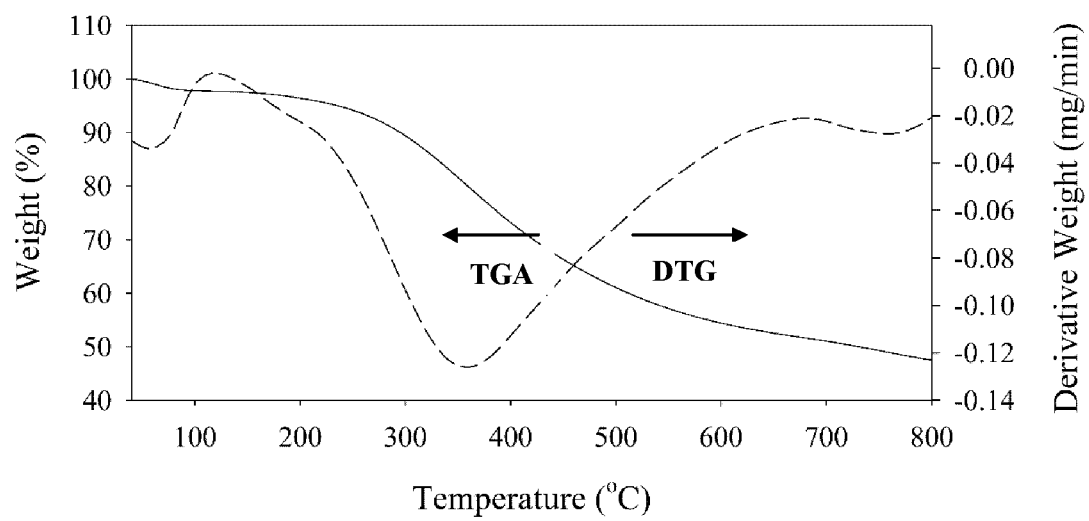
FIG. 10 shows the TGA/DTG graphs for the insoluble humins by-product with the solid line representing TGA plotting weight % versus temperature and the broken line representing DTG plotting derivative weight (mg/min) versus temperature.

Thermogravimetric analysis (TGA) and derivative thermogravimetry (DTG) of the insoluble humin by-product showed that thermal decomposition of the humin sample in nitrogen atmosphere starts at 265° C. and levels off at around 700° C. (FIG. 10). The total mass loss of the sample was 52.6 wt %, representing the volatile matter (VM) content of the humin by-product. The fixed carbon (FC) and ash content (AC) were further measured to be 46.5 wt % and 0.87 wt %, respectively, by switching the atmosphere from nitrogen to air at 800° C. for 10 min to burn the carbon residue. According to the DTG graph, the major thermal degradation peak temperature for the humin by-product was observed at around 350° C.

In summary, the present disclosure provides a novel and cost-effective continuous-flow process/technology as well as a novel and inexpensive method for preparation of heterogeneous solid catalysts for production of HMF at high selectivity and yield by catalytic conversion of various carbohydrate feedstocks such as, but not limited to simple $C_6$-based sugars and industrial-grade sugar syrups derived from starch (such as HFCS from corn starch) and cellulosic biomass (such as TMP-Bio Sugar from hydrolysis of aspen wood) in a novel continuous-flow tubular reactor in an aqueous/organic bi-phasic media using novel inexpensive heterogeneous solid catalysts.

The novel bi-phasic continuous-flow reactor possesses some unique aspects/features which make it ideal for scale-up and industrial application. These features include:

The system is easy and simple to operate and catalyst load/discharge and provides simultaneously an in-situ extraction of the product to the organic phase/solvent continuously and as soon as produced while two immiscible liquid phases (bi-phasic media) are flowing co-currently through the tubular flow reactor. The system also possesses the capability to adjust the residence/retention time of each phase (aqueous and organic) independently and aqueous to organic phase ratio (NO) inside the flow reactor easily by changing the flow rate of each phase, compared with batch reactor process where the residence time of feedstock (aqueous phase) and the residence time of the organic phase (which extract the majority of the desirable final product) are always identical. This enables increasing the feedstock conversion by decreasing the aqueous phase flow rate (i.e., increasing the residence time of the feedstock inside the flow reactor) while achieving a high final product selectivity and yield by increasing the organic phase flow rate (i.e., decreasing the residence time of the final product inside the flow reactor and suppressing the side-reactions).

Additionally, the system provides effective preheating of the bi-phasic liquid media inside the reactor and efficient temperature control; therefore, uniform temperature distribution of the flowing bi-phasic liquid along the tubular flow reactor is facilitated. The system also provides the possibility of in-situ catalyst regeneration and reuse as well as adjusting the reaction pressure independent of the temperature using a back-pressure regulator valve (despite the batch reactors where the pressure of the system depends on the reaction temperature). The system is also appropriate and applicable for different reactions and processes and allows the feasibility of installing several reactors in parallel to increase the capacity and continue the process with the fresh/regenerated catalyst column(s) while the used catalyst column(s) is/are under regeneration process.

Another novel aspect of this disclosure is development of various inexpensive but very active heterogeneous solid catalysts prepared with a simple and green method—i.e., solid-solid grinding of catalyst precursor compounds at room temperature. The catalysts demonstrated to be recyclable and reusable after regeneration for the HMF production process. This novel method for preparation of heterogeneous solid catalysts is simple, convenient and inexpensive, gives a high yield of product and involves less solvent and reduces contamination compared to known and conventional methods such as wet-chemical synthesis techniques.

Another novel aspect of this disclosure is using different grades of High Fructose Corn Syrup (HFCS) and sugar syrups derived from hydrolysis of wood as feedstocks for production of HMF. The present process provides the capability to convert different industrial-grade sugars, such as syrups derived from hydrolysis of starch and crop residues or woody biomass, directly into HMF.

The present process possesses a combination of several significant features and advantages compared with the existing/reported processes, as follows.

Using a continuous-flow bi-phasic tubular reactor disclosed herein, enables large-scale industrial and commercial production of HMF.

Using niobium phosphate (NbP) as an inexpensive mineral and commercial catalyst as well as developing a novel, inexpensive, solvent-free and green method for synthesis of heterogeneous tin phosphate (SnP) catalyst (prepared through a simple solid-solid grinding of tin and phosphorus salts at room temperature, offering a high yield of SnP catalyst with a high purity), enables large-scale application and production of inexpensive catalysts for the HMF production process or other processes.

Using water as an inexpensive and green solvent for the sugar feedstock, enables direct utilization of inexpensive industrial-grade sugar syrups derived from hydrolysis of starch (such as High Fructose Corn Syrup from corn starch) or cellulose (such as TMP-Bio Sugar from Aspen wood) without the need of pure sugars. This eliminates the expensive operations required for extracting pure/crystalline sugar, which is otherwise needed in many existing sugar-to-HMF conversion processes using organic solvents or ionic liquids as reaction media.

Using an organic solvent (e.g., MIBK) as an extracting agent to continuously extract the produced HMF from the aqueous medium in-situ while flowing through the tubular flow reactor enhances the HMF selectivity and yield by suppressing the side reactions of HMF in water medium. Pure 5-HMF can be obtained after simple evaporation/condensation of the extracting organic solvent and recycling the organic solvent back to the reactor.

Using NaCl (an inexpensive inorganic salt) as the phase transfer catalyst (PTC) increases the HMF selectivity and yield by enhancing the partition coefficient of HMF towards the organic phase (salting-out effect).

Thus, the present process achieves high selectivity and yield of HMF by suppressing the production of a variety of undesirable by-products and has a great potential for upscaling to the large industrial/commercial scale.

The foregoing description of the preferred embodiments of the invention has been presented to illustrate the principles of the invention and not to limit the invention to the particular embodiment illustrated. It is intended that the scope of the invention be defined by all of the embodiments encompassed within the following claims and their equivalents.

REFERENCES

[1] Takagaki, A.; Ohara, M.; Nishimura, S.; Ebitani, K. One-Pot Formation of Furfural from Xylose via Isomerization and Successive Dehydration Reactions over Heterogeneous Acid and Base Catalysts. Chem. Lett. 2010, 39 (8), 838-840.

[2] Pagan-Torres, Y. J.; Wang, T.; Gallo, J. M. R.; Shanks, B. H.; Dumesic, J. A. Production of 5-Hydroxymethylfurfural from Glucose Using a Combination of Lewis and Brønsted Acid Catalysts in Water in a Biphasic Reactor with an Alkylphenol Solvent. ACS Catalysis. 2012, 2 (6), 930-934.

[3] Ohara, M.; Takagaki, A.; Nishimura, S.; Ebitani, K. Syntheses of 5-Hydroxymethylfurfural and Levoglucosan by Selective Dehydration of Glucose Using Solid Acid and Base Catalysts. Appl. Catal. A Gen. 2010, 383 (1-2), 149-155.

[4] Román-Leshkov, Y.; Dumesic, J. a. Solvent Effects on Fructose Dehydration to 5-Hydroxymethylfurfural in Biphasic Systems Saturated with Inorganic Salts. Top. Catal. 2009, 52 (3), 297-303.

[5] Takagaki, A.; Ohara, M.; Nishimura, S.; Ebitani, K. A One-Pot Reaction for Biorefinery: Combination of Solid Acid and Base Catalysts for Direct Production of 5-Hydroxymethylfurfural from Saccharides. Chem. Commun. 2009, No. 41, 6276-6278.

[6] Yu, S.; Kim, E.; Park, S.; Song, I. K.; Jung, J. C. Isomerization of Glucose into Fructose over Mg–Al Hydrotalcite Catalysts. Catal. Commun. 2012, 29, 63-67.

[7] Yuan, Z.; Xu, C. C.; Cheng, S.; Leitch, M. Catalytic Conversion of Glucose to 5-Hydroxymethyl Furfural Using Inexpensive Co-Catalysts and Solvents. Carbohydr. Res. 2011, 346 (13), 2019-2023.

[8] McNeff, C. V.; Nowlan, D. T.; McNeff, L. C.; Yan, B.; Fedie, R. L. Continuous Production of 5-Hydroxymethylfurfural from Simple and Complex Carbohydrates. Appl. Catal. A Gen. 2010, 384 (1-2), 65-69.

[9] Brasholz, M.; von Känel, K.; Hornung, C. H.; Saubern, S.; Tsanaktsidis, J. Highly Efficient Dehydration of Carbohydrates to 5-(Chloromethyl) Furfural (CMF), 5-(Hydroxymethyl) Furfural (HMF) and Levulinic Acid by Biphasic Continuous Flow Processing. Green Chem. 2011, 13 (5), 1114-1117.

[10] Kuster, B. F. M. 5-Hydroxymethylfurfural (HMF). A Review Focusing on Its Manufacture. Starch/Staerke 1990, 42, 314-321.

[11] Putten, R. Van; Waal, J. C. Van Der; Jong, E. De; Rasrendra, C. B.; Heeres, H. J.; Vries, J. G. De. Hydroxymethylfurfural, A Versatile Platform Chemical Made from Renewable Resources. Chem. Rev. 2013, 113 (3), 1499-1597.

[12] Torres, A. I.; Daoutidis, P.; Tsapatsis, M. Continuous Production of 5-Hydroxymethylfurfural from Fructose: A Design Case Study. Energy Environ. Sci. 2010, 3 (10), 1560-1572.

[13] Yang, F.; Liu, Q.; Bai, X.; Du, Y. Conversion of Biomass into 5-Hydroxymethylfurfural Using Solid Acid Catalyst. Bioresour. Technol. 2011, 102 (3), 3424-3429.

[14] Rosatella, A. A.; Simeonov, S. P.; Frade, R. F. M.; Afonso, C. a. M. 5-Hydroxymethylfurfural (HMF) as a Building Block Platform: Biological Properties, Synthesis and Synthetic Applications. Green Chem. 2011, 13 (4), 754-793.

[15] Aida, T. M.; Sato, Y.; Watanabe, M.; Tajima, K.; Nonaka, T.; Hattori, H.; Arai, K. Dehydration of D-Glucose in High Temperature Water at Pressures up to 80 MPa. J. Supercrit. Fluids 2007, 40 (3), 381-388.

[16] Carlini, C.; Giuttari, M.; Maria Raspolli Galletti, A.; Sbrana, G.; Armaroli, T.; Busca, G. Selective Saccharides Dehydration to 5-Hydroxymethyl-2-Furaldehyde by Heterogeneous Niobium Catalysts. Appl. Catal. A Gen. 1999, 183 (2), 295-302.

[17] Asghari, F. S.; Yoshida, H. Dehydration of Fructose to 5-Hydroxymethylfurfural in Sub-Critical Water over Heterogeneous Zirconium Phosphate Catalysts. Carbohydr. Res. 2006, 341 (14), 2379-2387.

[18] Su, Y.; Brown, H. M.; Huang, X.; Zhou, X. dong; Amonette, J. E.; Zhang, Z. C. Single-Step Conversion of Cellulose to 5-Hydroxymethylfurfural (HMF), a Versatile Platform Chemical. Appl. Catal. A Gen. 2009, 361 (1-2), 117-122.

[19] Zhao, S.; Cheng, M.; Li, J.; Tian, J.; Wang, X. One Pot Production of 5-Hydroxymethylfurfural with High Yield from Cellulose by a Brønsted-Lewis-Surfactant-Combined Heteropolyacid Catalyst. Chem. Commun. (Camb). 2011, 47 (7), 2176-2178.

[20] Ordomsky, V. V.; Van Der Schaaf, J.; Schouten, J. C.; Nijhuis, T. A. Fructose Dehydration to 5-Hydroxymethylfurfural over Solid Acid Catalysts in a Biphasic System. ChemSusChem 2012, 5 (9), 1812-1819.

[21] Qi, X.; Watanabe, M.; Aida, T. M.; Smith, R. L. Catalytical Conversion of Fructose and Glucose into 5-Hydroxymethylfurfural in Hot Compressed Water by Microwave Heating. Catal. Commun. 2008, 9 (13), 2244-2249.

[22] Daorattanachai, P.; Namuangruk, S.; Viriya-empikul, N.; Laosiripojana, N.; Faungnawakij, K. 5-Hydroxymethylfurfural Production from Sugars and Cellulose in Acid- and Base-Catalyzed Conditions under Hot Compressed Water. J. Ind. Eng. Chem. 2012, 18 (6), 1893-1901.

[23] Guan, J.; Cao, Q.; Guo, X.; Mu, X. The Mechanism of Glucose Conversion to 5-Hydroxymethylfurfural Catalyzed by Metal Chlorides in Ionic Liquid: A Theoretical Study. Comput. Theor. Chem. 2011, 963 (2-3), 453-462.

[24] Nakajima, K.; Baba, Y.; Noma, R.; Kitano, M.; Kondo, J.; Hayashi, S.; Hara, M. Nb2O5·nH2O as a Heterogeneous Catalyst with Water-Tolerant Lewis Acid Sites. J. Am. Chem. Soc. 2011, 133, 4224-4227.

[25] Wang, T.; Glasper, J. A.; Shanks, B. H. Kinetics of Glucose Dehydration Catalyzed by Homogeneous Lewis Acidic Metal Salts in Water. Appl. Catal. A Gen. 2015, 498, 214-221.

[26] Lanzafame, P.; Temi, D. M.; Perathoner, S.; Spadaro, A. N.; Centi, G. Direct Conversion of Cellulose to Glucose and Valuable Intermediates in Mild Reaction Conditions over Solid Acid Catalysts. Catal. Today 2012, 179 (1), 178-184.

Therefore, what is claimed is:

1. A method for production of 5-hydroxymethyl furfural (5-HMF) from feedstock containing any one or combination of simple $C_6$-based sugars, industrial-grade sugar syrups and sugars derived from starch and/or cellulosic biomass, comprising:

continuously flowing a bi-phasic reaction medium including water, an organic solvent and the feedstock through an elongate tubular reactor having located therein a packed-bed column of heterogeneous solid catalyst containing any one or combination of Brønsted acid sites and Lewis acid sites, the packed-bed column extending along a preselected length of the said elongate tubular reactor, the packed-bed column of heterogeneous solid catalyst having first and second opposed ends located within the tubular reactor;

heating the elongate tubular reactor to a preselected temperature suitable for inducing reaction between a particular feedstock and a particular heterogenous solid catalyst;

monitoring temperatures of the first and second opposed ends of the packed-bed column and controlling and maintaining the temperature of the elongate tubular reactor such that the temperatures of the first and second opposed ends are within about 10° C. of each other;

operating the elongate tubular reactor at a pressure sufficiently high to prevent boiling of the water and the organic solvent at the preselected temperature such that the feedstock undergoes reaction to form 5-hydroxymethyl furfural in aqueous phase; and continuously and in-situ extracting the produced 5-hydroxymethyl furfural (HMF) from the aqueous phase to the organic phase/solvent as soon as produced while flowing through the tubular reactor.

2. The method according to claim 1 wherein the heterogeneous solid catalyst is any one or combination of a metal phosphate, a metal oxide modified with an acid group and a heteropoly acid.

3. The method according to claim 2 wherein the metal phosphate is any one of a phosphate of Nb, Sn, Ti, V, Cr, Zr, Al, Ga, Fe, Hf, and Ta.

4. The method according to claim 2 wherein the metal phosphate is any one of anhydrous and hydrated niobium phosphate ($NbOPO_4$), and anhydrous or hydrated tin phosphate ($Sn(HPO_4)_2$).

5. The method according to claim 2 wherein the metal oxide is any one of $TiO_2$, $ZrO_2$, $Nb_2O_5$, $Al_2O_3$, $SnO_2$, $HfO_2$, and $Ta_2O_5$.

6. The method according to claim 2 wherein the heteropoly acid is any one of $H_3PW_{12}O_{40}$, $H_4SiW_{12}O_{40}$ and $H_3PMo_{12}O_{40}$.

7. The method according to claim 1, wherein the organic solvent is any one or combination of a cyclic ether, a non-polar organic solvent, a ketone, an alcohol, and an aromatic organic solvent.

8. The method according to claim 1, wherein the organic solvent is methyl isobutyl ketone or tetrahydrofuran.

9. The method according to claim 1, wherein the feedstock comprises fructose, and wherein the catalyst is one of Niobium phosphate (NbP) and Amberlyst 36 (Amb. 36), and wherein the organic solvent is methyl isobutyl ketone (MIBK) or tetrahydrofuran (THF), and wherein the temperature is maintained in a range from about 110° C. to about 150° C.

10. The method according to claim 1, wherein the feedstock comprises fructose, and wherein the catalyst is niobium phosphate (NbP), and wherein the organic solvent is methyl isobutyl ketone (MIBK) or tetrahydrofuran (THF), and wherein the temperature is maintained at about 150° C.

11. The method according to claim 1, wherein the feedstock comprises fructose, and wherein the catalyst is Amberlyst 36 (Amb. 36), and wherein the organic solvent is methyl isobutyl ketone (MIBK) or tetrahydrofuran (THF), and wherein the temperature is maintained at about 150° C.

12. The method according to any claim 1, wherein the feedstock comprises glucose, and wherein the catalyst is one of niobium phosphate (NbP) and tin phosphate (SnP), and wherein the organic solvent is methyl isobutyl ketone (MIBK) or tetrahydrofuran (THF), and wherein the temperature is maintained in a range from about 110° C. to about 150° C.

13. The method according to claim 1, wherein the feedstock comprises glucose, and wherein the catalyst is niobium phosphate (NbP), and wherein the organic solvent is methyl isobutyl ketone (MIBK) or tetrahydrofuran (THF), and wherein the temperature is maintained at about 150° C.

14. The method according to claim 1, wherein the feedstock comprises glucose, and wherein the catalyst is tin phosphate (SnP), and wherein the organic solvent is methyl isobutyl ketone (MIBK) or tetrahydrofuran (THF), and wherein the temperature is maintained at about 150° C.

15. The method according to claim 1, wherein the feedstock comprises an industrial-grade sugar syrup derived from corn and/or cellulosic biomass, and wherein the catalyst is niobium phosphate (NbP), and wherein the organic solvent is methyl isobutyl ketone (MIBK) or tetrahydrofuran (THF), and wherein the temperature is maintained in a range from about 110° C. to about 150° C.

16. The method according to claim 1, wherein the feedstock comprises an industrial-grade sugar syrup derived from corn and/or cellulosic biomass, and wherein the catalyst is niobium phosphate (NbP), and wherein the organic solvent is methyl isobutyl ketone (MIBK) or tetrahydrofuran (THF), and wherein the temperature is maintained at about 150° C.

17. The method according to claim 1, wherein the industrial-grade sugar syrup derived from corn and cellulosic biomass includes any one or combination of high fructose corn syrup (HFCS), glucose corn syrup and wood based sugar.

18. The method according to claim 1, wherein the temperatures of the first and second opposed ends of the elongate tubular reactor are within about 5 to 10° C. of each other.

19. The method according to claim 4 wherein the anhydrous or hydrated tin phosphate ($Sn(HPO_4)_2$) is made by solid-solid grinding of tin chloride pentahydrate ($SnCl_4.5H_2O$) and sodium dihydrogen phosphate dihydrate ($NaH_2PO_4.2H_2O$) powders at about room temperature to form a colourless thick viscous liquid followed by oven drying at about 60 to about 150° C. to produce a powder composition, washing the powder composition with water to remove sodium and chloride ions, followed by vacuum drying at about 60 to about 150° C., calcining the as-synthesized SnP catalyst at about 200 to 400° C. for about 2 to 8 hours.

20. The method according to claim 19 wherein the step of oven drying is carried out at about 100° C., and wherein the step of vacuum drying is carried out at about 60° C., and wherein the step of calcining is carried out at about 300° C. for about 4 hours.

21. A reactor system for production of 5-hydroxymethyl furfural (5-HMF) from feedstock containing any one or combination of simple $C_6$-based sugars, industrial-grade sugar syrups and sugars derived from starch and/or cellulosic biomass, comprising:
an elongate bi-phasic continuous-flow tubular reactor having located therein a packed-bed column of heterogeneous solid catalyst containing any one or combination of Brønsted acid sites and Lewis acid sites, said packed-bed column extending along a preselected length of said elongate tubular reactor, said packed-bed column of heterogeneous solid catalyst having first and second opposed ends located within the tubular reactor;
temperature sensors positioned to sense the temperature at each of said opposed ends of said packed-bed column of heterogeneous solid catalyst;
a heat conducting element enveloping the said elongate tubular reactor, a heat generator surface inside a column heater attached to said heat conductor envelope, a temperature controller coupled to said column heater for controlling an maintaining a preselected temperature in said elongate tubular reactor and programmed to maintain the temperatures of the first and second opposed ends to within about 10° C. of each other during operation;
a feedstock container and a first liquid pump for pumping aqueous liquid from said feedstock container;
an extracting solvent container and a second liquid pump for pumping extracting organic solvent from said extracting solvent container;
the first and second pumps being in flow communication with a reactor input passageway for flowing a bi-phasic mixture of aqueous feedstock and extracting organic solvent through said elongate tubular reactor and said packed-bed column of heterogeneous solid catalyst located therein;
a back-pressure regulator valve for regulating and controlling an internal pressure of the continuous-flow reactor, a pressure gauge for measuring the internal pressure; and
an output conduit leading from an output port on said elongate tubular reactor to a product container, and an in-line filter located on said output conduit to filter the bi-phasic liquid product of the reaction.

22. The system according to claim 21 wherein said heterogeneous solid catalyst is any one or combination of a metal phosphate, a metal oxide modified with an acid group and a heteropoly acid.

23. The system according to claim 22 wherein the metal phosphate is a phosphate of any one of Nb, Sn, Ti, V, Cr, Zr, Al, Ga, Fe, Hf, and Ta.

24. The system according to claim 22 wherein the metal phosphate is any one of anhydrous and hydrated niobium phosphate ($NbOPO_4$), wherein, and anhydrous and hydrated tin phosphate ($Sn(HPO_4)_2$).

25. The system according to claim 22 wherein the metal oxide is any one of $TiO_2$, $ZrO_2$, $Nb_2O_5$, $Al_2O_3$, $SnO_2$, $HfO_2$, and $Ta_2O_5$.

26. The system according to claim 22 wherein the heteropoly acid is any one of $H_3PW_{12}O_{40}$, $H_4SiW_{12}O_{40}$ and $H_3PMo_{12}O_{40}$.

27. A method of producing a heterogeneous catalyst for use in a continuous-flow tubular reactor having an internal diameter of the tubular reactor D, comprising:
solid-solid grinding of any one of powders of anhydrous or hydrated tin phosphate ($Sn(HPO_4)_2$), anhydrous or hydrated zirconium phosphate, anhydrous or hydrated hafnium phosphate, anhydrous or hydrated chromium phosphate, anhydrous or hydrated tantalum phosphate and anhydrous or hydrated niobium phosphate together with sodium dihydrogen phosphate dihydrate ($NaH_2PO_4.2H_2O$) powders at about room temperature to form a colourless thick viscous liquid followed by oven drying at about 60 to about 150° C. to produce a powder composition, washing the powder composition with water to remove sodium and chloride ions, followed by vacuum drying at about 60 to about 150° C., calcining the as-synthesized catalyst at about 200 to 400° C. for about 2 to 8 hours, and crushing and sieving to obtain heterogeneous catalyst particles having a size $d_p$ in a range of $6<D/d_p<30$.

28. The method according to claim 1, wherein the tubular reactor has an internal diameter of the tubular reactor D, and wherein the heterogeneous solid catalysts have a particle size $d_p$ in a range of $6<D/d_p<30$, where D is the inner diameter of the tubular reactor used.

29. The system according to claim 21, wherein the tubular reactor has an internal diameter of the tubular reactor D, and wherein the heterogeneous solid catalysts have a particle size $d_p$ in a range of $6<D/d_p<30$.

30. A method for production of 5-hydroxymethyl furfural (5-HMF) from feedstock containing any one or combination of simple $C_6$-based sugars, industrial-grade sugar syrups and sugars derived from starch and/or cellulosic biomass, comprising:
continuously flowing a bi-phasic reaction medium including water, an organic solvent and the feedstock through an elongate tubular reactor having located therein a packed-bed column of heterogeneous solid catalyst containing any one or combination of Brønsted acid sites and Lewis acid sites and being any one or combination of a metal phosphate, a metal oxide modified with an acid group and a heteropoly acid, wherein the heteropoly acid is any one of $H_3PW_{12}O_{40}$, $H_4SiW_{12}O_{40}$ and $H_3PMo_{12}O_{40}$, the packed-bed column extending along a preselected length of the said elongate tubular reactor, the packed-bed column of heterogeneous solid catalyst having first and second opposed ends located within the tubular reactor;
heating the elongate tubular reactor to a preselected temperature suitable for inducing reaction between a particular feedstock and a particular heterogenous solid catalyst;
monitoring temperatures of the first and second opposed ends of the packed-bed column and controlling and maintaining the temperature of the elongate tubular reactor such that the temperatures of the first and second opposed ends are within about 10° C. of each other;
operating the elongate tubular reactor at a pressure sufficiently high to prevent boiling of the water and the organic solvent at the preselected temperature such that the feedstock undergoes reaction to form 5-hydroxymethyl furfural in aqueous phase; and continuously and in-situ extracting the produced 5-hydroxymethyl furfural (HMF) from the aqueous phase to the organic phase/solvent as soon as produced while flowing through the tubular reactor.

31. A reactor system for production of 5-hydroxymethyl furfural (5-HMF) from feedstock containing any one or combination of simple $C_6$-based sugars, industrial-grade sugar syrups and sugars derived from starch and/or cellulosic biomass, comprising:

an elongate bi-phasic continuous-flow tubular reactor having located therein a packed-bed column of heterogeneous solid catalyst containing any one or combination of Brønsted acid sites and Lewis acid sites and being any one or combination of a metal phosphate, a metal oxide modified with an acid group and a heteropoly acid, wherein the heteropoly acid is any one of $H_3PW_{12}O_{40}$, $H_4SiW_{12}O_{40}$ and $H_3PMo_{12}O_{40}$, said packed-bed column extending along a preselected length of said elongate tubular reactor, said packed-bed column of heterogeneous solid catalyst having first and second opposed ends located within the tubular reactor;

temperature sensors positioned to sense the temperature at each of said opposed ends of said packed-bed column of heterogeneous solid catalyst;

a heat conducting element enveloping the said elongate tubular reactor, a heat generator surface inside a column heater attached to said heat conductor envelope, a temperature controller coupled to said column heater for controlling an maintaining a preselected temperature in said elongate tubular reactor and programmed to maintain the temperatures of the first and second opposed ends to within about 10° C. of each other during operation;

a feedstock container and a first liquid pump for pumping aqueous liquid from said feedstock container;

an extracting solvent container and a second liquid pump for pumping extracting organic solvent from said extracting solvent container;

the first and second pumps being in flow communication with a reactor input passageway for flowing a bi-phasic mixture of aqueous feedstock and extracting organic solvent through said elongate tubular reactor and said packed-bed column of heterogeneous solid catalyst located therein;

a back-pressure regulator valve for regulating and controlling an internal pressure of the continuous-flow reactor, a pressure gauge for measuring the internal pressure; and an output conduit leading from an output port on said elongate tubular reactor to a product container, and an in-line filter located on said output conduit to filter the bi-phasic liquid product of the reaction.

32. A method for production of 5-hydroxymethyl furfural (5-HMF) from feedstock containing fructose, comprising:

continuously flowing a bi-phasic reaction medium including water, methyl isobutyl ketone (MIBK) or tetrahydrofuran (THF) organic solvent and the fructose feedstock through an elongate tubular reactor having located therein a packed-bed column of heterogeneous solid catalyst Amberlyst 36 (Amb. 36), the packed-bed column extending along a preselected length of the said elongate tubular reactor, the packed-bed column of heterogeneous solid catalyst having first and second opposed ends located within the tubular reactor;

heating the elongate tubular reactor to a preselected temperature in a range from about 110° C. to about 150° C. suitable for inducing reaction between a particular feedstock and a particular heterogenous solid catalyst;

monitoring temperatures of the first and second opposed ends of the packed-bed column and controlling and maintaining the temperature of the elongate tubular reactor such that the temperatures of the first and second opposed ends are within about 10° C. of each other;

operating the elongate tubular reactor at a pressure sufficiently high to prevent boiling of the water and the organic solvent at the preselected temperature such that the feedstock undergoes reaction to form 5-hydroxymethyl furfural in aqueous phase; and continuously and in-situ extracting the produced 5-hydroxymethyl furfural (HMF) from the aqueous phase to the organic phase/solvent as soon as produced while flowing through the tubular reactor.

33. The method according to claim 32, wherein the temperature is maintained at about 150° C.

* * * * *